US011178934B2

(12) United States Patent
Smith et al.

(10) Patent No.: US 11,178,934 B2
(45) Date of Patent: Nov. 23, 2021

(54) RESILIN MATERIAL FOOTWEAR AND FABRICATION METHODS

(71) Applicant: Bolt Threads Inc., Emeryville, CA (US)

(72) Inventors: Matthew Jordan Smith, Emeryville, CA (US); Michael Eun-Suk Lee, Berkeley, CA (US); Mitchell Joseph Heinrich, Oakland, CA (US); Paul James Jehlen, Richmond, CA (US)

(73) Assignee: Bolt Threads Inc., Emeryville, CA (US)

( * ) Notice: Subject to any disclaimer, the term of this patent is extended or adjusted under 35 U.S.C. 154(b) by 95 days.

(21) Appl. No.: 16/513,135

(22) Filed: Jul. 16, 2019

(65) Prior Publication Data

US 2020/0022451 A1 Jan. 23, 2020

Related U.S. Application Data

(60) Provisional application No. 62/700,197, filed on Jul. 18, 2018.

(51) Int. Cl.
| | |
|---|---|
| *A43B 13/02* | (2006.01) |
| *A43B 13/04* | (2006.01) |
| *A43B 3/12* | (2006.01) |
| *A43B 13/18* | (2006.01) |
| *A43B 13/12* | (2006.01) |
| *C07K 14/435* | (2006.01) |
| *C08J 3/24* | (2006.01) |
| *C08J 9/00* | (2006.01) |

(Continued)

(52) U.S. Cl.
CPC .............. *A43B 13/04* (2013.01); *A43B 3/128* (2013.01); *A43B 13/127* (2013.01); *A43B 13/186* (2013.01); *A43B 13/188* (2013.01); *A43B 17/003* (2013.01); *C07K 14/43563* (2013.01); *C08J 3/247* (2013.01); *C08J 9/0066* (2013.01); *C08J 9/04* (2013.01); *C08J 2389/00* (2013.01)

(58) Field of Classification Search
CPC ....... A43B 13/04; A43B 13/02; A43B 13/186; A43B 13/188; A43B 13/38; A43B 17/003
USPC ................................................ 36/25 R, 30 R
See application file for complete search history.

(56) References Cited

U.S. PATENT DOCUMENTS

| | | | | |
|---|---|---|---|---|
| 4,016,661 A | * | 4/1977 | Tibbitts .................... | A43B 3/02 36/4 |
| 4,439,937 A | * | 4/1984 | Daswick ................ | A43B 13/10 36/107 |

(Continued)

FOREIGN PATENT DOCUMENTS

| | | |
|---|---|---|
| KR | 1020170113209 A | 10/2017 |
| WO | 2015068160 A1 | 5/2015 |

OTHER PUBLICATIONS

Qin, Guokui et al., "Mechanism of resilin elasticity", Nature Communications, Aug. 14, 2012 (publication date), vol. 3, Article No. 1003, https://www.nature.com/articles/ncomms2004.

(Continued)

*Primary Examiner* — Marie D Bays
(74) *Attorney, Agent, or Firm* — Price Heneveld LLP

(57) ABSTRACT

An article of footwear includes an upper and a midsole coupled with the upper. The midsole includes at least a portion of a solid resilin material comprising a cross-linked recombinant resilin and a polar nonaqueous solvent.

18 Claims, 12 Drawing Sheets

(51) Int. Cl.
*C08J 9/04* (2006.01)
*A43B 17/00* (2006.01)

(56) References Cited

U.S. PATENT DOCUMENTS

| | | | | |
|---|---|---|---|---|
| RE33,066 E | * | 9/1989 | Stubblefield | A43B 7/144 36/83 |
| 7,810,252 B2 | * | 10/2010 | Stone | A43B 13/26 36/4 |
| 2004/0211089 A1 | * | 10/2004 | Boncutter | A43B 5/08 36/30 R |
| 2005/0091881 A1 | * | 5/2005 | Burgess | A43B 13/20 36/30 R |
| 2006/0026863 A1 | * | 2/2006 | Liu | A43B 13/16 36/25 R |
| 2006/0277795 A1 | * | 12/2006 | Baier | A43B 13/026 36/30 R |
| 2007/0275408 A1 | * | 11/2007 | Elvin | C07K 14/43581 435/7.1 |
| 2008/0256828 A1 | * | 10/2008 | Doran | A43B 9/00 36/88 |
| 2010/0242306 A1 | * | 9/2010 | Fu | A43B 13/189 36/102 |
| 2010/0263228 A1 | * | 10/2010 | Kang | A43B 13/187 36/29 |
| 2012/0090077 A1 | * | 4/2012 | Brown | A41B 11/007 2/239 |
| 2015/0133593 A1 | | 5/2015 | Kissell et al. | |
| 2015/0223560 A1 | * | 8/2015 | Wawrousek | A43D 1/02 36/25 R |
| 2016/0135537 A1 | * | 5/2016 | Wawrousek | A43B 13/141 36/28 |
| 2019/0125030 A1 | * | 5/2019 | Brown | A43B 13/04 |

OTHER PUBLICATIONS

Kim, Yeji et al., "Enzymatic Cross-Linking of Resilin-Based Proteins for Vascular Tissue Engineering Applications", Biomacromolecules, Jul. 11, 2016 (Publication date), vol. 17, No. 8, pp. 2530-2539, School of Chemical Engineering and Weldon School of Biomedical Engineering, Purdue University, West Lafayette, Indiana, United States.

Elvin, Christopher M. et al., "Snythesis and Properties of Cross-linked Recombinant Pro-Resilin", Nature, Oct. 13, 2005 (Publication date), vol. 437, pp. 999-1002, Nature Publishing Group.

* cited by examiner

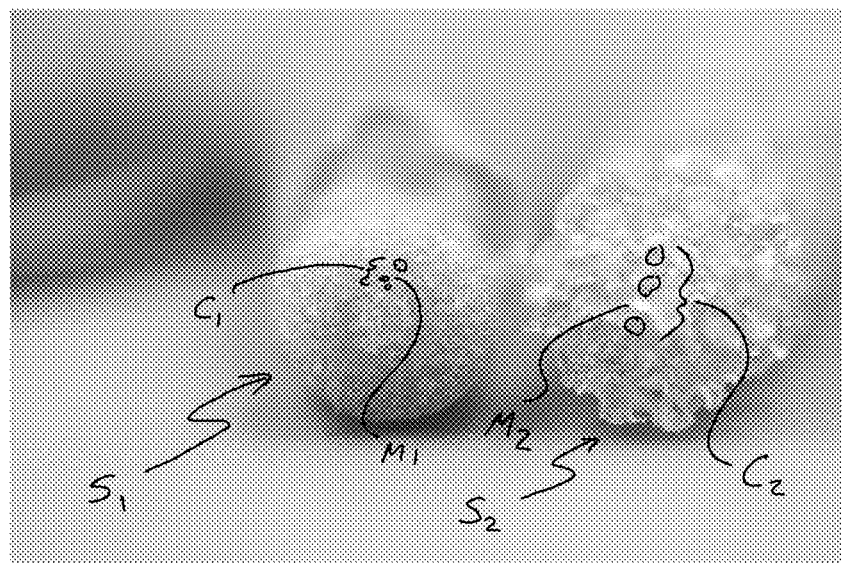
FIG. 4
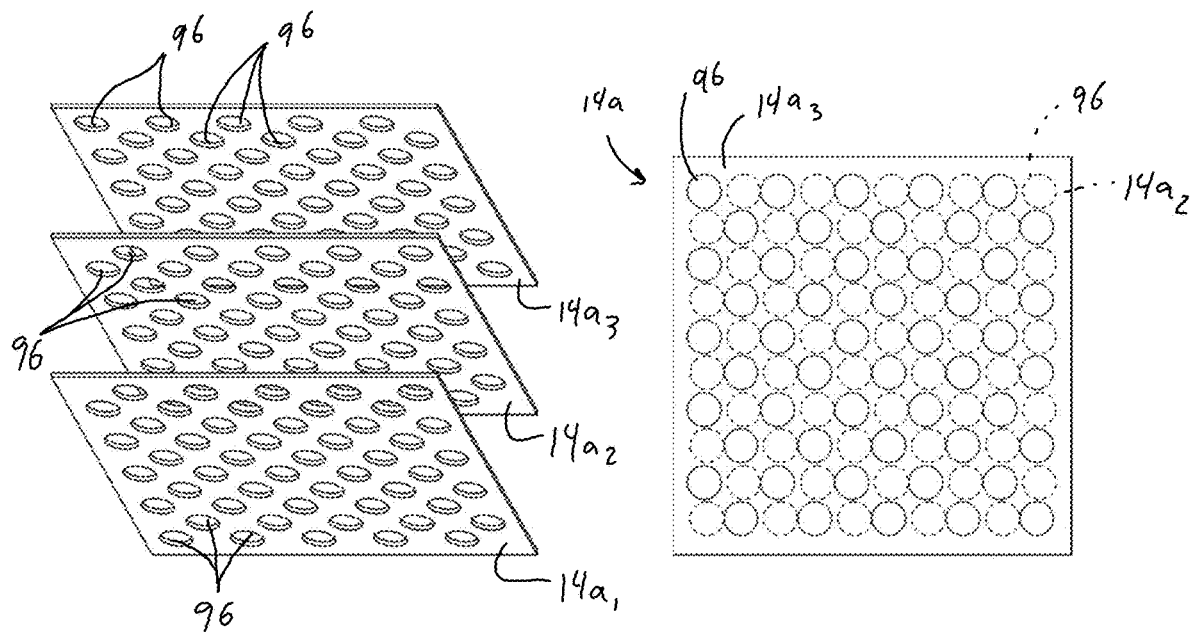
FIG. 5A
FIG. 5B

RESILIN MATERIAL FOOTWEAR AND FABRICATION METHODS

This application claims the benefit of U.S. Provisional Application No. 62/700,197, entitled "Cross-Linked Elastomeric Proteins in Polar Nonaqueous Solvents and Uses Thereof," filed on Jul. 18, 2018, the contents of which are incorporated by reference in their entirety.

This application is related to International Application No. PCT/US2018/013839, filed Jan. 16, 2018, which claims benefit of U.S. Provisional Application No. 62/446,230, filed on Jan. 13, 2017, the contents of which are each incorporated in their entirety.

BACKGROUND

The present disclosure generally relates to footwear fabricated, at least in part, using a solid resilin material comprising a cross-linked recombinant resilin and a polar nonaqueous solvent.

Due to its potential characteristics with respect to elastic efficiency, compressive elastic modulus, tensile elastic modulus, shear modulus, hardness, rebound, and compression set, resilin is of increasing interest in generating materials. Resilins have many unique properties compared to petroleum-based elastomers. In particular, resilin is a protein, and therefore can be biodegraded, which makes it more environmentally friendly than petroleum-based polymers. Also, resilin is biocompatible and can therefore be used in applications that involve contact with humans or animals. Lastly, the mechanical properties of recombinant resilins can be tuned through varying protein sequence, protein structure, amount of intermolecular cross-linking and processing variables to produce elastomers designed for a universe of specific applications.

The usability of specifically processed solid resilin material as alternative to petroleum-based elastomers makes it particularly suitable for use in goods and articles typically made from or incorporating such elastomers. In one application footwear, including various types of sneakers, incorporate different elastomers in various ways. Resilin compositions and methods of making the same that have desirable mechanical properties and are suitable for large-scale, efficient production are disclosed in co-pending, commonly-assigned U.S. Provisional Pat. No. 62/700,197, the entire disclosure of which is incorporated by reference herein. What is needed are solid resilin materials suited for the various portions of footwear that have been or can be made from elastomer, as well as configurations for such portions of footwear and methods for their fabrication that utilize the unique properties of resilin.

SUMMARY

In at least one aspect of the disclosure, an article of footwear includes an upper and a midsole coupled with the upper. The midsole includes at least a portion of a solid resilin material comprising a cross-linked recombinant resilin and a polar nonaqueous solvent.

In various embodiments, the solid resilin material may be an elastomer that defines at least one physical property resembling that of a petroleum-based elastomer. In one example, the petroleum-based elastomer may be ethyl vinyl acetate foam.

In an additional or alternative embodiment, the midsole may define at least one exposed ground-contacting surface. The at least one exposed ground contacting surface may be in one of the heel or fore-foot areas of the midsole and may, further be uncovered by an outsole.

In various embodiments the article of footwear can be a sneaker, further including a lasting board, the upper being affixed with the lasting board to define an interior foot-receiving cavity therewith, and the midsole being coupled with the upper opposite the lasting board. In a further embodiment, the article of footwear can be a sandal, and the upper can include one or more straps and defines at least one open area.

In at least another aspect, a method for making an article of footwear includes placing a purified recombinant resilin composition in a mold with a cross-linking solution, incubating the recombinant resilin composition in the cross-linking solution to generate a solid resilin material, fabricating a midsole including at least a portion of the solid resilin material, and assembling the midsole with an upper. In various embodiments, the method can further comprise, prior to fabricating the midsole, subjecting the solid resilin material to a solvent exchange process to substantially remove the cross-linking solution and configure the solid resilin material as a solid resilin material comprising a cross-linked recombinant resilin and a polar nonaqueous solvent.

In at least another aspect, an insole for an article of footwear includes a solid resilin material comprising a cross-linked recombinant resilin and a polar nonaqueous solvent and defining at least a portion of the insole. In an embodiment, the portion of the insole comprising the solid resilin material can include an exposed foot-supporting surface. Additionally or alternatively, the portion of the insole comprising the solid resilin material can define an overall shape of the insole.

These and other features, advantages, and objects of the present device will be further understood and appreciated by those skilled in the art upon studying the following specification, claims, and appended drawings.

BRIEF DESCRIPTION OF THE DRAWINGS

The foregoing summary, as well as the following detailed description of the invention, will be better understood when read in conjunction with the appended drawings. For the purpose of illustration, there are shown in the drawings, certain aspects of the disclosure. It should be understood, however, that the disclosure is not limited to the precise arrangements and instrumentalities shown. Drawings are not necessarily to scale. Certain features of the invention may be exaggerated in scale or shown in schematic form in the interest of clarity and conciseness.

In the drawings:

FIG. 4 is a front perspective view of two samples of foamed resilin material;

FIGS. 5A and 5B are exploded perspective and top elevation views of a laminated perforated structure of solid resilin material;

DETAILED DESCRIPTION OF EMBODIMENTS

Figure 1:
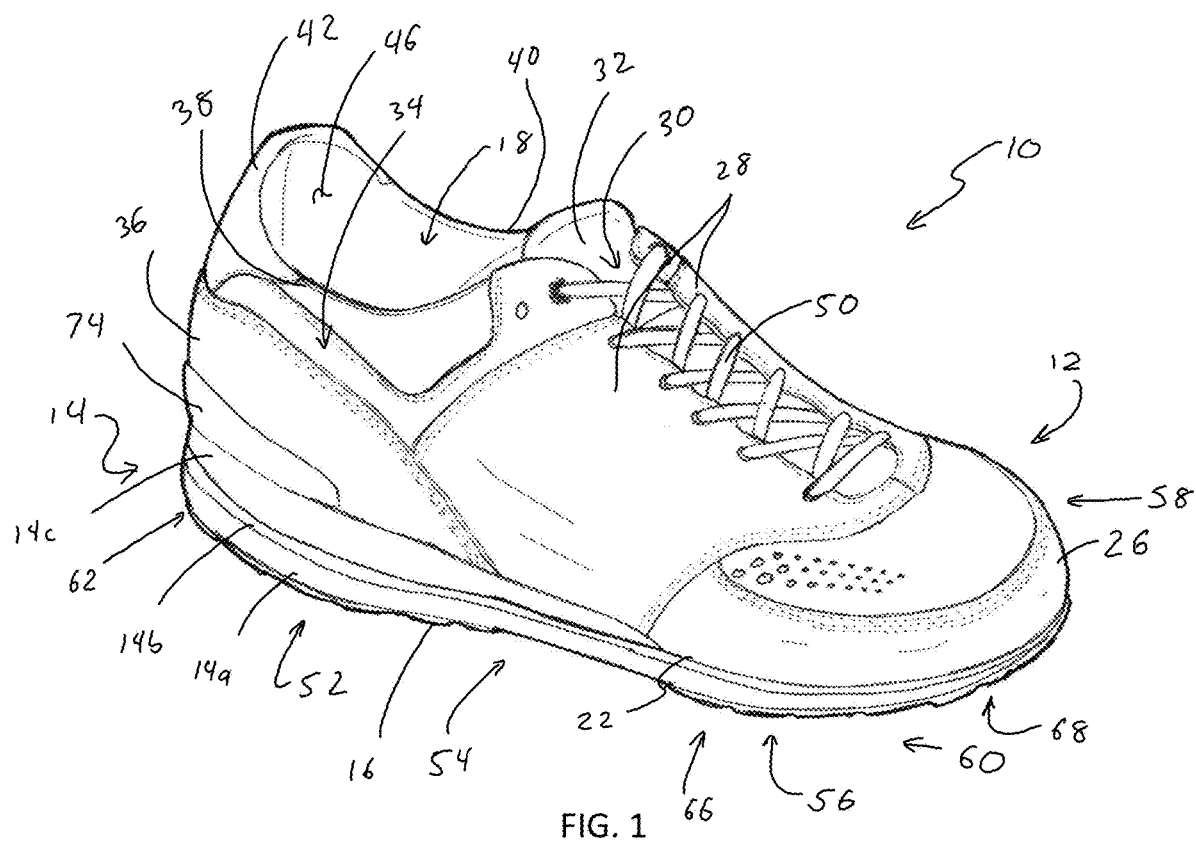
FIG. 1 is a front perspective view of a sneaker according to an aspect of the disclosure.

The details of various embodiments of the invention are set forth in the description below. Other features, objects, and advantages of the invention will be apparent from the description and the drawings, and from the claims.

Definitions

Unless defined otherwise, all technical and scientific terms used herein have the same meaning as is commonly understood by one of ordinary skill in the art to which this disclosure pertains.

The terms "a" and "an" and "the" and similar referents as used herein refer to both the singular and the plural, unless otherwise indicated herein or clearly contradicted by context.

The term "about," "approximately," or "similar to" means within an acceptable error range for the particular value as determined by one of ordinary skill in the art, which can depend in part on how the value is measured or determined, or on the limitations of the measurement system. It should be understood that all ranges and quantities described below are approximations and are not intended to limit the invention. Where ranges and numbers are used these can be approximate to include statistical ranges or measurement errors or variation. In some embodiments, for instance, measurements could be plus or minus 10%.

Amino acids can be referred to by their single-letter codes or by their three-letter codes. The single-letter codes, amino acid names, and three-letter codes are as follows: G—Glycine (Gly), P—Proline (Pro), A—Alanine (Ala), V—Valine (Val), L—Leucine (Leu), I—Isoleucine (Ile), M—Methionine (Met), C—Cysteine (Cys), F—Phenylalanine (Phe), Y—Tyrosine (Tyr), W—Tryptophan (Trp), H—Histidine (His), K—Lysine (Lys), R—Arginine (Arg), Q—Glutamine (Gln), N—Asparagine (Asn), E—Glutamic Acid (Glu), D—Aspartic Acid (Asp), S—Serine (Ser), T—Threonine (Thr).

The terms "including," "includes," "having," "has," "with," or variants thereof are intended to be inclusive in a manner similar to the term "comprising."

The term "microbe" as used herein refers to a microorganism, and refers to a unicellular organism. As used herein, the term includes all bacteria, all archaea, unicellular protista, unicellular animals, unicellular plants, unicellular fungi, unicellular algae, all protozoa, and all chromista.

The term "native" as used herein refers to compositions found in nature in their natural, unmodified state.

The terms "optional" or "optionally" mean that the feature or structure may or may not be present, or that an event or circumstance may or may not occur, and that the description includes instances where a particular feature or structure is present and instances where the feature or structure is absent, or instances where the event or circumstance occurs and instances where the event or circumstance does not occur.

The term "secreted fraction" as used herein refers to the fraction of recombinant resilins that are secreted from cells compared to the total resilins produced by the cells.

The term "secretion signal" as used herein refers to a short peptide that when fused to a polypeptide mediates the secretion of that polypeptide from a cell.

The term "secreted resilin coding sequence" as used herein refers to a nucleotide sequence that encodes a resilin as provided herein fused at its N-terminus to a secretion signal and optionally at its C-terminus to a tag peptide or polypeptide.

The term "recombinant" as used herein in reference to a polypeptide (e.g., resilin) refers to a polypeptide that is produced in a recombinant host cell, or to a polypeptide that is synthesized from a recombinant nucleic acid.

The term "recombinant host cell" as used herein refers to a host cell that comprises a recombinant nucleic acid.

The term "recombinant nucleic acid" as used herein refers to a nucleic acid that is removed from its naturally occurring environment, or a nucleic acid that is not associated with all or a portion of a nucleic acid abutting or proximal to the nucleic acid when it is found in nature, or a nucleic acid that is operatively linked to a nucleic acid that it is not linked to in nature, or a nucleic acid that does not occur in nature, or a nucleic acid that contains a modification that is not found in that nucleic acid in nature (e.g., insertion, deletion, or point mutation introduced artificially, e.g., by human intervention), or a nucleic acid that is integrated into a chromosome at a heterologous site. The term includes cloned DNA isolates and nucleic acids that comprise chemically-synthesized nucleotide analog.

The term "vector" as used herein refers to a nucleic acid molecule capable of transporting another nucleic acid to which it has been linked. One type of vector is a "plasmid," which generally refers to a circular double stranded DNA loop into which additional DNA segments can be ligated, but also includes linear double-stranded molecules such as those resulting from amplification by the polymerase chain reaction (PCR) or from treatment of a circular plasmid with a restriction enzyme. Other vectors include bacteriophages, cosmids, bacterial artificial chromosomes (BAC), and yeast artificial chromosomes (YAC). Another type of vector is a viral vector, wherein additional DNA segments can be ligated into the viral genome. Certain vectors are capable of autonomous replication in a cell into which they are introduced (e.g., vectors having an origin of replication that functions in the cell). Other vectors can be integrated into the genome of a cell upon introduction into the cell, and are thereby replicated along with the cell genome.

The term "repeat" as used herein, in reference to an amino acid or nucleic acid sequence, refers to a sub-sequence that is present more than once in a polynucleotide or polypeptide (e.g., a concatenated sequence). A polynucleotide or polypeptide can have a direct repetition of the repeat sequence without any intervening sequence, or can have non-consecutive repetition of the repeat sequence with intervening sequences. The term "quasi-repeat" as used herein, in reference to amino acid or nucleic acid sequences, is a sub-sequence that is inexactly repeated (i.e., wherein some portion of the quasi-repeat subsequence is variable between quasi-repeats) across a polynucleotide or polypeptide. Repeating polypeptides and DNA molecules (or portions of polypeptides or DNA molecules) can be made up of either repeat sub-sequences (i.e., exact repeats) or quasi-repeat sub-sequences (i.e., inexact repeats).

The term "native resilin" as used herein refers to an elastomeric polypeptide or protein produced by insects. GenBank Accession Nos. of non-limiting examples of native resilin includes the following NCBI sequence numbers: XP 002034179 (*Drosophila sechellia*), NP 995860 (*Drosophila melanogaster*), NP 611157 (*Drosophila melanogaster*), Q9V7U0 (*Drosophila melanogaster*), AAS64829, AAF57953 (*Drosophila melanogaster*), EGI57805, AEQ49438, XP003399675, AEQ49434, AEQ49437, XP 012058333, XP 006563165, XP 011184157, XP 001843145, XP 015011737, XP 008209097, XP 001605137, XP 002428637, XP 011165933, NP 001182329, XP 014220291, and ADM26717.

The term "modified" as used herein refers to a protein or polypeptide sequence that differs in composition from a native protein or polypeptide sequence, where the functional properties are preserved to within 10% of the native protein or polypeptide properties. In some embodiments, the difference between the modified protein or polypeptide and the native protein or polypeptide can be in primary sequence (e.g., one or more amino acids are removed, inserted or substituted) or post-translation modifications (e.g., glycosylation, phosphorylation). Amino acid deletion refers to removal of one or more amino acids from a protein. Amino acid insertion refers to one or more amino acid residues being introduced in a protein or polypeptide. Amino acid insertions may comprise N-terminal and/or C-terminal fusions as well as intra-sequence insertions of single or multiple amino acids. Amino acid substitution includes non-conservative or conservative substitution, where conservative amino acid substitution tables are well known in the art (see for example Creighton (1984) Proteins. W. H. Freeman and Company (Eds)). In some embodiments, the modified protein or polypeptide and the native protein or polypeptide amino acid or nucleotide sequence identity is at least 60%, at least 65%, at least 70%, at least 75%, at least 80%, at least 85%, at least 90%, at least 95%, or at least 98% of the amino acids or nucleotide bases.

The term "truncated" as used herein refers to a protein or polypeptide sequence that is shorter in length than a native protein or polypeptide. In some embodiments, the truncated protein or polypeptide can be greater than 10%, or greater than 20%, or greater than 30%, or greater than 40%, or greater than 50%, or greater than 60%, or greater than 70%, or greater than 80%, or greater than 90% of the length of the native protein or polypeptide.

The term "homolog" or "substantial similarity," as used herein, when referring to a polypeptide, nucleic acid or fragment thereof, indicates that, when optimally aligned with appropriate amino acid or nucleotide insertions or deletions with another amino acid or nucleic acid (or its complementary strand), there is amino acid or nucleotide sequence identity in at least 60%, at least 65%, at least 70%, at least 75%, at least 80%, at least 85%, at least 90%, at least 95%, or at least 98% of the amino acids or nucleotide bases, as measured by any well-known algorithm of sequence identity, such as FASTA, BLAST or Gap, as discussed above.

The term "resilin" as used herein refers to a protein or a polypeptide, capable of cross-linking to form an elastomer, where the protein or polypeptide is a native resilin, or a native resilin that is modified, or a native resilin that is truncated. Resilins of the present invention are preferably recombinant resilins. In some embodiments, recombinant resilins comprise a natural or modified (e.g., truncated or concatenated) nucleotide sequence coding for resilin or resilin fragments (e.g., isolated from insects), heterologously expressed and secreted from a host cell. In preferred embodiments, the secreted recombinant resilin protein is collected from a solution extracellular to the host cell.

As used herein, the term "elastomer" refers to a polymer with viscoelasticity and typically weak inter-molecular forces (except for covalent cross-links between molecules, if they are present). Viscoelasticity is a property of materials that exhibit both viscous and elastic characteristics when undergoing deformation, and therefore exhibit time-dependent strain. Elasticity is associated with bond stretching along crystallographic planes in an ordered solid, and viscosity is the result of the diffusion of atoms or molecules inside an amorphous material. Elastomers that are viscoelastic, therefore, generally have low Young's modulus and high failure strain compared with other materials. Due to the viscous component of the material, viscoelastic materials dissipate energy when a load is applied and then removed. This phenomenon is observed as hysteresis in the stress-strain curve of viscoelastic materials. As a load is applied there is a particular stress-strain curve, and as the load is removed the stress-strain curve upon unloading is different than that of the curve during loading. The energy dissipated is the area between the loading and unloading curves.

As used herein, the term "nonaqueous" refers to a solvent that predominantly comprises one or more compounds that are not water. This includes compositions that have undergone a solvent exchange process with a solvent that results in an overall decrease in the proportion of water present as a solvent, i.e., water has been replaced by non-water molecules as a solvent. In some embodiments, a nonaqueous solvent is one that comprises less than 50% water. A polar nonaqueous solvent, as used herein with respect to solvents for cross-linked resilin compositions, refers to any nonaqueous solvent that is capable of dissolving resilin.

As used herein, the term "coupled" (in all of its forms, couple, coupling, coupled, etc.) generally means the joining of two components directly or indirectly to one another. Such joining may be stationary in nature or movable in nature. Such joining may be achieved with the two components and any additional intermediate members being integrally formed as a single unitary body with one another or with the two components (e.g., the upper may be coupled to the outsole directly or through the midsole positioned therebetween). Such joining may be permanent in nature or may be removable or releasable in nature unless otherwise stated.

Recitation of ranges of values herein are merely intended to serve as a shorthand method of referring individually to each separate value inclusively falling within the range, unless otherwise indicated herein, and each separate value is incorporated into the specification as if it were individually recited herein.

When referring to the drawings, it is to be understood that the depicted article may assume various alternative orientations, except where expressly specified to the contrary. It is also to be understood that the specific articles, components, and processes illustrated in the attached drawings, and described in the following specification are simply exemplary of the concepts defined in the appended claims. Hence, specific dimensions and other physical characteristics relating to the embodiments disclosed herein are not to be considered as limiting, unless the claims expressly state otherwise. The details of various embodiments are set forth in the description below. Other features, objects, and advantages will be apparent from the description. Unless otherwise defined herein, scientific and technical terms used shall have the meanings that are commonly understood by those of ordinary skill in the art. Further, unless otherwise required by context, singular terms shall include the plural and plural terms shall include the singular. The terms "a" and "an" includes plural references unless the context dictates otherwise. Generally, nomenclatures used in connection with, and techniques of, biochemistry, enzymology, molecular and cellular biology, microbiology, genetics and protein and nucleic acid chemistry and hybridization described herein are those well-known and commonly used in the art.

Exemplary methods and materials are described below, although methods and materials similar or equivalent to those described herein can also be used and will be apparent to those of skill in the art. All publications and other references mentioned herein are incorporated by reference in their entirety. In case of conflict, the present specification, including definitions, will control. The materials, methods, and examples are illustrative only and not intended to be limiting.

Referring to the embodiment illustrated in FIG. 1, reference numeral 10 generally designates an article of footwear, specifically in the form of a sneaker. The sneaker 10 includes an upper 12 and a midsole 14 affixed with the upper 12. The midsole 14 includes at least a portion of a resilin material comprising a cross-linked recombinant resilin solid and a polar nonaqueous solvent.

Recombinant Resilin Materials and Production Methods

Provided herein is an overview of general compositions comprising recombinant resilins, and methods for their production that, unless otherwise indicated, may be common among various end-products that may use recombinant resilins, including those described below. These compositions and methods are generally similar to those described in the above-referenced '197 Application. In this respect, examples and details regarding the various aspects of the compositions and methods furthering the present disclosure are described therein.

Resilins have many unique properties compared to petroleum-based elastomers. Most notably, at least in its many naturally-occurring applications, resilin has an extreme elastic efficiency (i.e., resilience), where very little of the energy input into deformation is lost as heat. Other desirable properties of resilin relate to, for example, resilin's compressive elastic modulus, tensile elastic modulus, shear modulus, hardness, rebound, and compression set. Moreover, resilin is a protein, and therefore can be biodegraded, which makes it more environmentally friendly than petroleum-based polymers. Also, resilin is biocompatible and can therefore be used in applications that involve contact with humans or animals. Lastly, the mechanical properties of recombinant resilins can be tuned through varying protein sequence, protein structure, amount of intermolecular cross-linking and processing variables to produce elastomers designed for a universe of specific applications.

Described herein are various cross-linked resilin compositions with various mechanical properties and methods of producing them. Also provided herein are methods of cross-linking resilin compositions to form various examples of a cross-linked resilin solid that can be performed in large batches and results in little to no degradation from impurities left over from the cross-linking reaction in comparison to previous methods. In some examples, the cross-linking reaction comprises exposure of the resilin to a persulfate, such as ammonium persulfate. Heat can be applied to initiate a cross-linking reaction catalyzed by persulfate. In some examples, cross-linking occurs in vessels or molds such that the recombinant resilin compositions obtained have specific shapes or forms, as discussed in the various practical examples discussed below and shown in the figures.

The cross-linked resilin solid compositions provided herein also include cross-linked resilin compositions comprising a polar nonaqueous solvent to provide selected mechanical properties with respect to elastic modulus, hardness, maximum elastic compressive load, resilience, material lifetime/fatigue, or the like, that are determined to be suitable for use in certain applications, including in the examples of footwear, as discussed below. In some embodiments, the compositions are made by performing a solvent exchange with a resilin composition to replace an aqueous solvent with a nonaqueous solvent. In other applications, a solvent exchange may be made to replace a cross-linking solution or solvent with a solvent that is selected for the properties it contributes to a finished product, including resistance to degradation, that may not be realized by the cross-linking solution. Solvents that are capable of solvent exchange with cross-linked resilin include solvents that dissolve resilin in its non-cross-linked form.

In some examples, the nonaqueous solvent is non-volatile and water soluble or polar. In some embodiments, the molecular weight of the solvent is about 100 or less. In further examples, the polar nonaqueous solvent comprises non-volatile water miscible solvents mixed with water or used as neat solutions such as propylene glycol, glycerol, ethylene glycol, polyethylene glycol of various molecular weights from 400 to 1 million. In another example, the polar nonaqueous solvent may comprise B) Ionic liquids as neat solutions or mixed with water (in ratios from 70:30 IL:water to 30:70 IL:water) such as 1-ethyl-3-methylimidazolium acetate and 1-butyl-3-methylimidazolium bromide. Notably, 1-ethyl-3-methylimidazolium acetate not only dissolves resilin at 20 wt % when mixed 1:1 with water, but the crosslinking reaction can also be carried out in this solvent when mixed with water. This solution does not dehydrate over time due to the ionic liquid's hygroscopic nature. Examples of resilin materials with other polar nonaqueous solvents are possible, additional examples of which are given in the '197 Application.

Resilin Compositions

Examples of native resilin may contain an N-terminal A-domain comprising a plurality of repeat units comprising the consensus amino acid sequence YGXP ("A-repeat"), where X is any amino acid; a chitin-binding type RR-2 (C) domain; and a C-terminal B-domain comprising a plurality of repeat units comprising the consensus amino acid sequence UYZXZ ("B-repeat"), where U is glycine or serine; Z is serine, glycine, arginine, or proline; and X is any amino acid. Not all naturally occurring resilins have A-, C-, and B-domains. Native resilins produced by various insects typically have inexact repeats (i.e., quasi-repeats) within the A- and/or B-domains with some amino acid variation between the quasi-repeats. Various examples of recombinant resilins according to the present disclosure can similarly comprise one or more A-repeats and one or more B-repeats in various consensus sequences of motifs of amino acids and residues described in greater detail in the above-incorporated '197 application. Additionally, some examples of the recombinant resilins comprise one or more A-repeats, one or more B-repeats, and/or one or more C-domain. In further examples, the recombinant resilins comprise: one or more A-repeats or one or more B-repeats but not both; one or more A-repeats but not B-repeats or C-domains; one or more B-repeats but not A-repeats or C-domains. In examples in which the recombinant resilins comprise a C-domain, the C-domain can be situated either on the N-terminal or the C-terminal sides of the A-repeats or B-repeats, or between the A-repeats and the B-repeats. Some examples of the recombinant resilins may further comprise additional the sequences containing an amino acid, which may be located on the N-terminal side of an A-repeat or B-repeat.

In some examples, the recombinant resilins are full-length native resilins expressed in a non-native environment. In some embodiments, the recombinant resilins comprise a truncated version of native resilins. In some embodiments, the truncated native resilins comprise at least one A-repeat. In some embodiments, the truncated native resilins comprise at least one B-repeat. Non-limiting examples of full-length and truncated native resilins are provided in the above-referenced '197 Application. In some examples, the recombinant resilins are full-length or truncated native resilins that are cross-linked in a non-native manner (e.g., less or more cross-linking, cross-linking via different amino acid residues). In some of the examples, the recombinant resilins are modified full-length or native resilins that are truncated to various degrees.

In some examples, the modified resilins differ from full-length or truncated native resilins in amino acid residues that are post-translationally modified (e.g., glycosylated, phosphorylated) such that the modified resilins have one or more different locations and/or different amounts and/or different types of post-translational modifications than the full-length or truncated native resilins. In some embodiments, the modified resilins differ from full-length or truncated native resilins in amino acid residues that are involved in cross-linking such that the modified resilins have one or more different locations and/or different amounts and/or different types of amino acids that are involved in cross-linking than full-length or truncated native resilins. In some such embodiments, the modified resilins differ from the full-length or truncated native resilin in comprising one or more additional or fewer tyrosine residues, one or more additional or fewer lysine residues, and/or one or more additional or fewer cysteine residues.

In some examples, the recombinant resilins comprise concatenated native or truncated native resilins or concatenated modified resilins. In some examples, the concatenated native or truncated native resilins or concatenated modified resilins comprise at least 2 A-repeats (e.g., 2, 3, 4, 5, 6, 7, 8, 9, 10, or more). In some embodiments, the concatenated truncated native resilins or concatenated modified resilins comprise at least 2 B-repeats (e.g., 2, 3, 4, 5, 6, 7, 8, 9, 10, or more).

Cross-Linking

In some embodiments, the recombinant resilins can be cross-linked according to various methods to obtain specific recombinant resilin compositions. The recombinant resilin in the desired solvent with cross-linking agents can be filled into molds to achieve a desired shape of the resulting solid after cross-linking. Examples of resulting recombinant resilin solids are in FIGS. 1-15 and are discussed further below.

In various examples, cross-linking may be achieved via tyrosine residues to create di- and tri-tyrosine crosslinking in resilin to form a resilin solid. In other examples, cross linking can be achieved via lysine residues. In some examples, cross linking can be achieved via cysteine residues. In some examples, cross-linking may employ transglutaminase or poly(ethylene glycol) (PEG). In other examples, recombinant resilin can be cross-linked via enzymatic cross-linking (e.g., using horseradish peroxidase). While this method can efficiently cross-link large solutions of resilin, the resulting cross-linked product comprises covalently incorporated active enzyme in the cross-linked resilin solid. This may yields radical chain reactions that could cause degradation of the protein backbone of the resilin, if left in a resulting resilin solid. In other examples, recombinant resilin can be cross-linked via photochemical cross-linking, although such cross-linking may not be efficient for reactions where photoactivation throughout the mold is required.

Examples of additional cross-linking chemistries are disclosed in the '197 Application that may prevent degradation and make solid substances with some mechanical properties preferred for certain applications where the amount and form of energy absorption is important. In some such examples, recombinant resilin may be cross-linked via a solvent comprising ammonium persulfate (at various concentration) and application of heat (e.g., incubation at a temperature of about 80° C. for about 2.5 hours, with other examples of heats and incubation temperatures provided therein). In some examples, other persulfates may be used.

Solvent-Exchanged Resilin Solids

Cross-linked resilin can be formed in an aqueous solvent resulting in a composition that has a low hardness and elastic modulus that is less suitable for certain applications where energy absorption and stiffness are desired. In some examples, a solvent exchange may be performed on cross-linked resilin compositions to replace an aqueous solvent with a polar nonaqueous solvent to provide desired material properties. As discussed above, the polar nonaqueous solvent may comprise non-volatile water miscible solvents mixed with water or used as neat solutions such as propylene glycol, glycerol, ethylene glycol, polyethylene glycol of various molecular weights from 400 to 1 million. In another example, the polar nonaqueous solvent may comprise ionic liquids as neat solutions or mixed with water (in ratios from 70:30 IL:water to 30:70 IL:water) such as 1-ethyl-3-methylimidazolium acetate and 1-butyl-3-methylimidazolium bromide. As also discussed above, 1-ethyl-3-methylimidazolium acetate not only dissolves resilin at 20 wt % when mixed 1:1 with water, but the crosslinking reaction can also be carried out in this solvent when mixed with water. This solution does not dehydrate over time due to the ionic liquid's hygroscopic nature and low vapor pressure. As described herein, material properties of cross-linked resilin compositions, including elastic modulus, hardness, maximum elastic compressive load, resilience, and material lifetime/fatigue, can be tuned using solvent exchange. Solvents that are capable of doing solvent exchange with cross-linked resilin include solvents that dissolve resilin in its non-crosslinked form. Additionally, as discussed further below, the exchange of a low vapor pressure solvent for water also increases the duration of time for which the resilin material remains elastomeric, as resilin relies on a certain level of hydration to remain elastomeric. An aqueous solvent will evaporate over a relatively short duration of time, such that the resilin becomes a hard solid. Polar nonaqueous solvents are more resistant to evaporation, limiting the effects thereof on the resulting resilin material.

In some examples, a solvent exchange to replace an aqueous solvent of resilin with a polar nonaqueous solvent can be performed in the presence of heat, e.g., at a temperature of about 60° C. In some embodiments the solvent exchange process is performed in a solution containing at least 1×, at least 2×, at least 5×, at least 10×, or at least 20× the volume of exchange solvent relative to the resilin solid. In some embodiments, the solvent exchange is performed for at least 1 hour, at least 2 hours, at least 4 hours, at least 8 hours, at least 16 hours, at least 24 hours, or at least 48 hours. In some examples, glycerol, propylene glycol, ethylene glycol, or DMSO are used as exchange solvents for cross-linked resilin solid compositions.

In some examples, the choice of exchange solvent and the concentration used can be selected to achieve a desired tunable mechanical property, such as stiffness, abrasion resistance, and the like, from the solvent design. This can be selected depending on the desired application (e.g., shoe outers, golf balls, etc.). Further, examples of the cross-linked resilin compositions formed by the above solvent exchange process and in a nonaqueous solvent may be stable at room temperature for extended periods of time compared to water-based cross-linked resilin solids. Further water-based resilin solids may exhibit lower material strength compared to nonaqueous solvent-based resilin solids. Still further, the recombinant resilin compositions discussed herein may have an elastic modulus greater than cross-linked recombinant resilin in an aqueous solvent.

In some implementations, the cross-linked resilin compositions described herein can have a Shore 00 Hardness of 50 or more, 40 or more, 30 or more, 20 or more, 10 or more, from 10 to 50, 40, 30, or 20; from 20 to 50, 40, or 30; from 30 to 50 or 40; or from 40 to 50 (which can be measured according to ASTM D2240). In further examples, the recombinant resilin compositions may have a hardness of at least 10 (as measured using a Shore 00 Durometer via ASTM D2240) or a hardness of from about 10 to about 50 (as measured using a Shore 00 Durometer via ASTM D2240).

In further examples, the recombinant resilin compositions described herein may exhibit a rebound resilience from about 40% to about 60% (as measured by ASTM D7121). In further examples, the recombinant resilin compositions described herein may exhibit a compressive stress at 25% of about 6 psi to about 8 psi (as measured by ASTM D575). In further examples, the recombinant resilin compositions described herein may not undergo an elastic to plastic transition below 2 kN of compressive force (as measured by a Zwick compression test).

The solid material properties of the various specific resilin compositions achieved according to the above, such as resilience, compressive elastic modulus, tensile elastic modulus, shear modulus, extension to break, maximum tensile strength, hardness, stiffness, and rebound may be tuned based on the solvent used and how the solvent exchange is performed. The concentration of resilin in the resilin solid and the amount of full length resilin as a portion of total resilin can also be adjusted to affect the material properties of the cross-linked resilin solid composition. In various examples, solvent exchange to replace the water-based resilin composition (i.e, a cross-linked resilin composition in an aqueous solvent) with a polar nonaqueous-based resilin composition (i.e., a cross-linked resilin composition in a polar nonaqueous solvent), as described herein, may result in a stiffer material with a similar resilience and a similar elasticity.

Foamed Resilin Solids

In some embodiments, the recombinant resilin composition is a foam material. In some embodiments, a method of preparing the recombinant resilin foam, comprises: providing a cross-linked recombinant resilin solid composition in an aqueous solvent; exchanging said aqueous solvent with a polar nonaqueous solvent; and introducing one or more bubbles to the cross-linked recombinant resilin solid composition. Any method of introducing bubbles known in the art may be used herein. For instance, methods of introducing bubbles include, but are not limited to, vortexing, mixing, adding yeast, and chemical reactions. In some embodiments, the introducing the one or more bubbles may occur at the same time the cross-linked recombinant resilin solid composition is provided. In some embodiments, the introducing the one or more bubbles may occur after the cross-linked recombinant resilin solid composition is provided.

Blowing agents typically are introduced into polymeric material to make polymer foams in one of two ways. According to one technique, a chemical blowing agent is mixed with a polymer. The chemical blowing agent undergoes a chemical reaction in the polymeric material, typically under conditions in which the polymer is molten, causing formation of a gas. Chemical blowing agents generally are low molecular weight organic compounds that decompose at a particular temperature and release a gas such as nitrogen, carbon dioxide, or carbon monoxide.

Exemplary chemical blowing agents include, but are not limited to, sodium bicarbonate, potassium bicarbonate, ammonium, azodicarbonamide, isocyanate, hydrazine, isopropanol, 5-phenyltetrazole, triazole, 4,4'oxybis(benzenesulfonyl hydrazide) (OBSH), trihydrazine triazine (THT), hydrogen phosphate, tartaric acid, citric acid, and toluenesulphonyl semicarbazide (TSS).

In some embodiments, foaming agents, thickeners, and/or hardeners are added to the recombinant resilin solid. Exemplary foaming agents include, but are not limited to, xanthan gum, sodium dodecyl sulfate, ammonium lauryl sulfate, bovine serum albumin. Exemplary thickeners include, but are not limited to, fumed silica and xanthan gum. Exemplary hardeners include, but are not limited to, aliphatic polyamine, fatty polyamides, aromatic polyamine hardeners, anhydride hardeners, boron trifluoride hardeners, and curing agents (dicyandiamide).

According to another technique a physical blowing agent, i.e., a fluid that is a gas under ambient conditions, is injected into a molten polymeric stream to form a mixture. The mixture is subjected to a pressure drop, causing the blowing agent to expand and form bubbles (cells) in the polymer. In some embodiments, the pressure required is about 500 psi to about 2000 psi, e.g., about 600 psi to about 1000 psi, about 700 psi to about 1500 psi, and about 800 psi to about 2000 psi. In some embodiments, the pressure required is about 500 psi.

Exemplary physical blowing agents include, but are not limited to, chlorofluorocarbon (CFC), dissolved nitrogen, $N_2$, $CH_4$, $H_2$, $CO_2$, Ar, pentane, isopentane, hexane, methylene dichloride, and dichlorotetra-fluoroethane.

Mechanical Properties

Further examples of resilin compositions that may be derived by the present disclosure may have different properties compared to compositions comprising cross-linked resilins. In some examples, the compositions provided herein may have similar properties compared to synthetic elastic or elastomeric materials, including various foams and the like. Non-limited examples of such properties include resilience, compressive elastic modulus, tensile elastic modulus, shear modulus, hardness, rebound, and compression set. Parameters that can be modified to obtain compositions with specific mechanical properties include, for example, the length and/or sequence of the recombinant resilins, the extent and/or type of post-translational modifications of the recombinant resilins, the extent and/or type of cross-linking of the recombinant resilins and the nature of the solvent of the cross-linked resilin composition.

Mechanical properties such as maximum tensile strength, compressive elastic modulus, tensile elastic modulus, shear modulus, extension to break and resilience can be measured using many different types of tensile and compression systems that conduct stress-strain measurements on elastomeric samples. Various possible processes and methods for testing these properties and various values for the resilin compounds that can be derived according to the present disclosure are described in the '197 Application.

The compositions provided herein have a number of uses, including but not limited to applications in aerospace, automotive, sporting equipment, vibration isolation, footwear, and clothing among others. Some applications from these categories are listed as non-limiting examples. Due to the desirable elastic efficiency, resilin can be used as an energy storage device (e.g., a rubber band) for storing and recovering mechanical energy. Automobile suspension systems can be improved by application of resilin bushings to keep more tire contact on the road when going over bumps and through potholes at speed. Additionally, there are a number of sporting equipment applications for resilin with differently tuned mechanical properties including cores of golf balls, tennis racket grips, golf club grips, and table tennis paddles.

An application of particular interest is footwear due to the unique properties of resilin compositions provided herein. As an insole or midsole, resilin can improve the comfort and bioefficiency of shoes by cushioning the foot strike and restoring more of the energy from that footstrike as forward momentum. As a midsole, resilin can make up the entire midsole or be encapsulated within another material to complement its properties (e.g., an abrasion or wear resistant material, or a material tuned for traction). The resilin midsole can also contain a plurality of resilin materials with differently tuned mechanical properties that work in concert to provide enhanced performance (e.g., softer heel strike area and firmer arch support), as discussed further below.

Vectors, Host Cells, and Fermentations

As disclosed further in the '197 Application, recombinant host cells comprising disclosed vectors may be used in fermentations to produce resilin protein, including those according to the various sequences discussed above. In some examples, the vectors provided comprise secreted resilin coding sequences, which encode a resilin polypeptide fused at its N-terminus to a secretion signal and optionally at its C-terminus to a tag peptide or polypeptide. In some examples, the vectors comprise secreted resilin coding sequences that are codon-optimized for expression in a particular host cell.

As discussed further in the '197 Application, suitable secretion signals are secretion signals that mediate secretion of polypeptides in the recombinant host cells provided herein. The resilins encoded by the secreted resilin coding sequences can be further fused to tag peptides or polypeptides. In some examples, the vectors comprise single secreted resilin coding sequences, while in other examples, the vectors comprise 2 or more (e.g., 3, 4, or 5) secreted resilin coding sequences. The secreted resilin coding sequences may be identical. Alternatively, at least 2 of the secreted resilin coding sequences are not identical. When at least 2 of the secreted resilin coding sequences are not identical, the at least 2 secreted resilin coding sequences can differ from each other in the resilins and/or in the secretion signals and/or the optional tag peptides or polypeptides they encode.

In some examples, the vectors comprise promoters that are operably linked to the secreted resilin coding sequences such that they drive the expression of the secreted resilin coding sequences. In further examples, the vectors comprise terminators that are operably linked to the secreted resilin coding sequences such that they effect termination of transcription of the secreted resilin coding sequences. In examples in which the vectors comprise 2 or more resilin coding sequences, the 2 or more resilin coding sequences can be operably linked to the same promoters and/or terminators or to 2 or more different promoters and/or terminators.

The vectors provided can further comprise elements suitable for propagation of the vectors in recombinant host cells. Non-limiting examples of such elements include bacterial origins of replication and selection markers (e.g., antibiotic resistance genes, auxotrophic markers). Bacterial origins of replication and selection markers are known in the art. In some embodiments, the selection marker is a drug resistant marker. A drug resistant marker enables cells to detoxify an exogenously added drug that would otherwise kill the cell.

The vectors of the disclosure can further comprise targeting sequences that direct integration of the secreted resilin coding sequences to specific locations in the genome of host cells. Non-limiting examples of such targeting sequences include nucleotide sequences that are identical to nucleotide sequences present in the genome of a host cell.

Recombinant host cells can comprise the vectors described. In some examples, the vectors are stably integrated within the genome (e.g., a chromosome) of the recombinant host cells, e.g., via homologous recombination or targeted integration. In other examples, the vectors are not stably integrated within the genome of the recombinant host cells but rather are extrachromosomal. Recombinant host cells can be of mammalian, plant, algae, fungi, or microbe origin. It should be understood that the term "recombinant host cell" is intended to refer not only to the particular subject cell but to the progeny of such a cell. Because certain modifications may occur in succeeding generations due to either mutation or environmental influences, such progeny may not, in fact, be identical to the parent cell, but is still included within the scope of the term "recombinant host cell" as used herein. In some examples, the recombinant host cells may comprise genetic modifications that improve production of the recombinant resilins provided herein.

The recombinant host cells are generated by transforming cells of suitable origin with vectors. For such transformation, the vectors can be circularized or be linear. Recombinant host cell transformants comprising the vectors can be readily identified, e.g., by virtue of expressing drug resistance or auxotrophic markers encoded by the vectors that permit selection for or against growth of cells, or by other means (e.g., detection of light emitting peptide comprised in vectors, molecular analysis of individual recombinant host cell colonies, e.g., by restriction enzyme mapping, PCR amplification, or sequence analysis of isolated extrachromosomal vectors or chromosomal integration sites). In some examples, the recombinant host cells provided herein can produce high titers of the recombinant resilins provided herein.

Production and secretion of recombinant resilins can be influenced by the number of copies of the secreted resilin coding sequences comprised in the recombinant host cells and/or the rate of transcription of the secreted resilin coding sequences comprised in the recombinant host cells. In some examples, the recombinant host cells comprise a single secreted resilin coding sequence. In other examples, the recombinant host cells comprise 2 or more (e.g., 3, 4, 5, or more) secreted resilin coding sequences. In some examples, the recombinant host cells comprise secreted resilin coding sequences that can be operably linked to strong promoters.

The fermentations comprise recombinant host cells and a culture medium suitable for growing the recombinant host cells. The fermentations are obtained by culturing the recombinant host cells in culture media that provide nutrients needed by the recombinant host cells for cell survival and/or growth, and for secretion of the recombinant resilins. Such culture media typically contain an excess carbon source. Non-limiting examples of suitable carbon sources include monosaccharides, disaccharides, polysaccharides, and combinations thereof. Non-limiting examples of suitable monosaccharides include glucose, galactose, mannose, fructose, ribose, xylose, arabinose, ribose, and combinations thereof. Non-limiting examples of suitable disaccharides include sucrose, lactose, maltose, trehalose, cellobiose, and combinations thereof. Non-limiting examples of suitable polysaccharides include raffinose, starch, glycogen, glycan, cellulose, chitin, and combinations thereof. The resulting fermentation can comprise recombinant resilins in varying amounts.

Methods of Producing Recombinant Resilin

The recombinant resilins described herein can be produced according to various methods. Such methods are generally performed according to conventional methods well known in the art and as described in various general and more specific references that are cited and discussed throughout the '197 Application, unless otherwise indicated. In some embodiments, a method can be utilized to secrete resilin extracellularly from a host cell, which may comprises constructing a vector comprising a secreted resilin coding sequence, transforming the vector into a host cell, and then culturing the recombinant host cells to secrete resilin extracellularly. The secreted resilin may then be purified, and the purified resilin can then be cross-linked to form an elastomer. In some examples, the methods may include the step of transforming cells with vectors provided herein to obtain recombinant host cells provided herein. Methods for transforming cells with vectors are well-known in the art.

The methods may further include the step of culturing the recombinant host cells in culture media under conditions suitable for obtaining the fermentations. In some examples, the conditions and culture media are suitable to facilitate secretion of the recombinant proteins from the recombinant host cells into the culture media. Suitable culture media for use in these methods are known in the art, as are suitable culture conditions.

Purification can occur by a variety of methods known in the art for purifying secreted proteins from fermentations. Various examples of common steps in such methods include centrifugation (to remove cells) followed by precipitation of the proteins using precipitants or other suitable cosmotropes (e.g., ammonium sulfate). The precipitated protein can then be separated from the supernatant by centrifugation, and resuspended in a solvent (e.g., phosphate buffered saline ["PBS"]). The suspended protein can be dialyzed to remove the dissolved salts. Additionally, the dialyzed protein can be heated to denature other proteins, and the denatured proteins can be removed by centrifugation. Optionally, the purified recombinant resilins can be coacervated. Methods of purifying the secreted recombinant proteins from the fermentation can include various centrifugation steps in conjunction with solubilizing protein in a whole cell broth or cell pellet with known chaotropes such as urea or guanidine thiocyanate, examples of which are discussed in greater detail in the '197 Application. Such methods and steps, as well as other purification methods are known in the art and can be used to or adapted to purify resilin, as described herein. Further detail of one example method can be found in Kim, M., Elvin, C., Brownlee, A. & Lyons, R. High yield expression of recombinant pro-resilin: Lactose-induced fermentation in *E. coli* and facile purification. Protein Expr. Purif. 52, 230-236 (2007). Various adaptations and combinations of known methods may be made to purify resilin at scale according to the knowledge of one skilled in the art. Examples of specific solutions and solvents for cross-linking, and various specific combinations thereof are discussed above and in the '197 Application.

Overview of Example Products Using the Resilin Material

In some embodiments, the cross-linked resilin compositions described herein can be used to provide a composition having improved physical properties, including, e.g., for absorption of energy from an applied force as desired. In some embodiments, the cross-linked resilin compositions described herein can be used to replace rubber or other synthetic elastomers in existing products. In particular, some of the cross-linked resilin compositions provided herein can absorb a large amount of force, while not transitioning to an inelastic material.

In some embodiments, the cross-linked resilin compositions provided herein can be used as an outer for a shoe, including at least for portions of the midsole. In some embodiments, the cross-linked resilin compositions provided herein can be used as part of a core for a golf ball, softball, or the like. In other embodiments, the cross-linked resilin compositions provided herein can be used in handles or grips, e.g., for sports equipment such as golf clubs or tennis rackets, as bicycle grips or motorcycle grips, or as grips for tools and industrial uses such as hammers, nail guns, jackhammers, and any other tools where it is preferable to absorb and return energy. In some embodiments, the cross-linked resilin compositions provided herein can be used in brushings or dampenings, e.g., skate board trucks or hard drive platter vibration dampener. In some embodiments, the cross-linked resilin compositions can be used as material for wheels, such as for skate boards, roller blades, or scooters. In some embodiments, the cross-linked resilin compositions provided herein can be used for safety and protective gear, such as padding for protective equipment such as helmets, elbow or knee pads, shoulder pads, protective gloves, or hard hats, or as a protective outer layer to protect the skin from abrasions.

In some embodiments, the cross-linked resilin compositions provided herein can be used for automotive parts, e.g., suspension components such as bushings or shock absorbers, or for interior cushioning such as seat bolsters and lumbar support. In some embodiments, the cross-linked resilin compositions provided herein can be used for tires and inner tubes. In some embodiments, the cross-linked resilin compositions provided herein can be used for suberballs. In some embodiments, the cross-linked resilin compositions provided herein can be used for shoe insoles, midsoles, and outsoles. In some embodiments, the cross-linked resilin compositions provided herein can be used in a padded mat. In some embodiments, the cross-linked resilin compositions provided herein can be used for several types of gaskets or O-rings. In some embodiments, the cross-linked resilin compositions provided herein can be added to plastic items to increase their impact resistance. In some embodiments, the cross-linked resilin compositions provided herein can be used for protective cases, such as phone or tablet cases. In some embodiments, the cross-linked resilin compositions provided herein can be used for rubber stamps. In some embodiments, the cross-linked resilin compositions provided herein can be used for rollers. In some embodiments, the cross-linked resilin compositions provided herein can be used for rubber bands.

In some embodiments, the cross-linked resilin compositions provided herein can be used for shoe soles, basement flooring, noise protection for sound studios, car bumpers, cushion pads, door mats, yoga mats, drum pads, window wipers, car tires, fire hoses, electrical wiring insulation, rubber bands, rubber ducks, elastic gloves, cooking utensils, rain boots, teething toys, bicycle tires, watches, jars, gaskets, hair ties, flip-flops, phone cases, medicine balls, bouncy balls, seals for electronic devices to prevent contamination from water or dust, refrigerator or freezer door seals, seals to prevent air flow in or out of a chamber, trampolines, pacifiers, window seals, Halloween masks, garden hoses, table tennis rackets, conveyer belts, ducting, stamps, or balloons.

It is to be appreciated that the above-described fermentation, purification, cross-linking, and solvent-exchange steps, in various examples (including those discussed specifically above and those that may be apparent or derived based on the above description) are derived or adapted to produce a resilin-based material generally resembling various elastomers. To that end, such processing steps can be particularly applied to produce specific resilin-based materials having characteristics or properties (including tactile, visual, and physical, as described in greater detail herein) similar to those of various elastomers, including elastomers of various types or having various known properties or attributes. In this manner, resilin-based material can be fermented, purified, cross-linked, solvent exchanged, or subjected to various post-processing steps according to the processes and variations described herein and in various combinations to produce raw-material that can be manufactured or fabricated into different products typically, or in various forms, being primarily of, or otherwise featuring or including, an elastomer. In certain forms and compositions, this resilin based material may result in products or articles that meet or exceed consumer, retailer, or manufacturer expectations for similar products of or including elastomer. In this manner, such products comprised of, using, or incorporating the various types of resilin material that may be produced according to or in light of the above description may provide benefits to the consumer and manufacturer beyond what is possible with traditional elastomers and in addition to the ecological, environmental, and humanitarian benefits that may be realized by substituting the resilin materials described herein for leather.

Footwear Including Resilin Compositions

In accordance with the preceding description, in one example, the resilin material described herein can be incorporated into in various types and forms of footwear, including in any of the various portions of footwear (among the various types thereof discussed herein and that would be understood based on the description herein) that can be, or typically are, formed of elastomeric material, including in substitution for various types of petroleum-based elastomers (e.g., ethyl vinyl acetate ("EVA")). In various forms, the resilin material described herein can be used for all or portions of a shoe "outer" for many types of shoes, as well as various portions of a shoe upper or, for some types of footwear, the entire upper. In such instances, specific implementations of the resilin compositions described herein can be used to derive materials having appropriate characteristics and can be used for the various elastomeric portions of an article of footwear with such resilin materials being fabricated or manufactured into the desired form, according to the particular footwear portion or component, various, non-limiting examples of which are discussed herein.

Referring to the embodiment illustrated in FIG. 1, reference numeral 10 generally designates a shoe, particularly in the form of a sneaker. As discussed herein, the term "sneaker", when used in reference to a type of footwear, connotes a style and construction capable of many practical variations, including with respect to particular stylistic implementations thereof and the particular construction within a generally accepted framework. Still further, sneakers can be designed and constructed for different types of activities or use, with various types of sneakers exhibiting ranges of stylistic or functional versatility making them suited for certain ranges of activities and use of varying scope.

In this respect, the shoe 10 illustrated in FIG. 1 may be characterized as an "athletic" sneaker, wherein the use of the term "athletic" in connection with the term "sneaker" to describe the depicted style of footwear does not imply or require that such footwear be strictly used or otherwise useable for any specific type of athletic activity, or for any athletics at all. In one example, an article of footwear may simply be of the style or construction of or evoking athletic footwear so as to encompass such footwear, whether used or intended for athletic activity or not (e.g., "lifestyle", "athleisure", or fashion-footwear styled as or similar to athletic sneakers or other variations of athletic footwear, as described below). Further, the descriptions made herein, including in reference to the drawing figures, are merely exemplary with respect to the footwear described and illustrated, so that variations may be made to the footwear described herein for purposes of style or fit and/or to make footwear based on the principles and construction described herein suitable for various purposes or conditions. Even further, although construction and production techniques may be discussed herein with respect to particular styles of footwear (e.g. athletic sneakers), such construction and production techniques discussed with respect to one type of footwear may be an acceptable alternative for comparable construction and production techniques discussed herein with respect to other types of footwear (e.g., hiking boots, sandals (including sport sandals), athleisure, lifestyle, and the like).

Continuing with reference to FIG. 1, the illustrated sneaker 10 is exemplary of typical construction of sneakers and includes an upper 12, a midsole 14, and an outsole 16, with the upper 12 defining an interior 18 generally suited for receiving the foot of a wearer, and the outsole 16 forming the portion of the sneaker 12 contacting the ground beneath the foot of the wearer. In this respect, the construction of the depicted sneaker 10 is generally typical of other types of footwear with it being noted that the combined midsole 14 and outsole 16 may be collectively referred to as the footwear "outer" and may be used in various forms other than the depicted midsole 14 and outsole 16. In one example, an outer may consist of a midsole of resilin material that exhibits acceptable abrasion resistance such that at least portions of the ground-contacting surface typically included in a separate outsole may be formed in the midsole of the resilin material, as discussed further below. As shown in the example of FIG. 1, the midsole 14 is positioned between the upper 12 and the outsole 16 and provides support and cushioning for the sole of the foot, particularly during impact with the ground, as made by the outsole 16.

Figure 2:
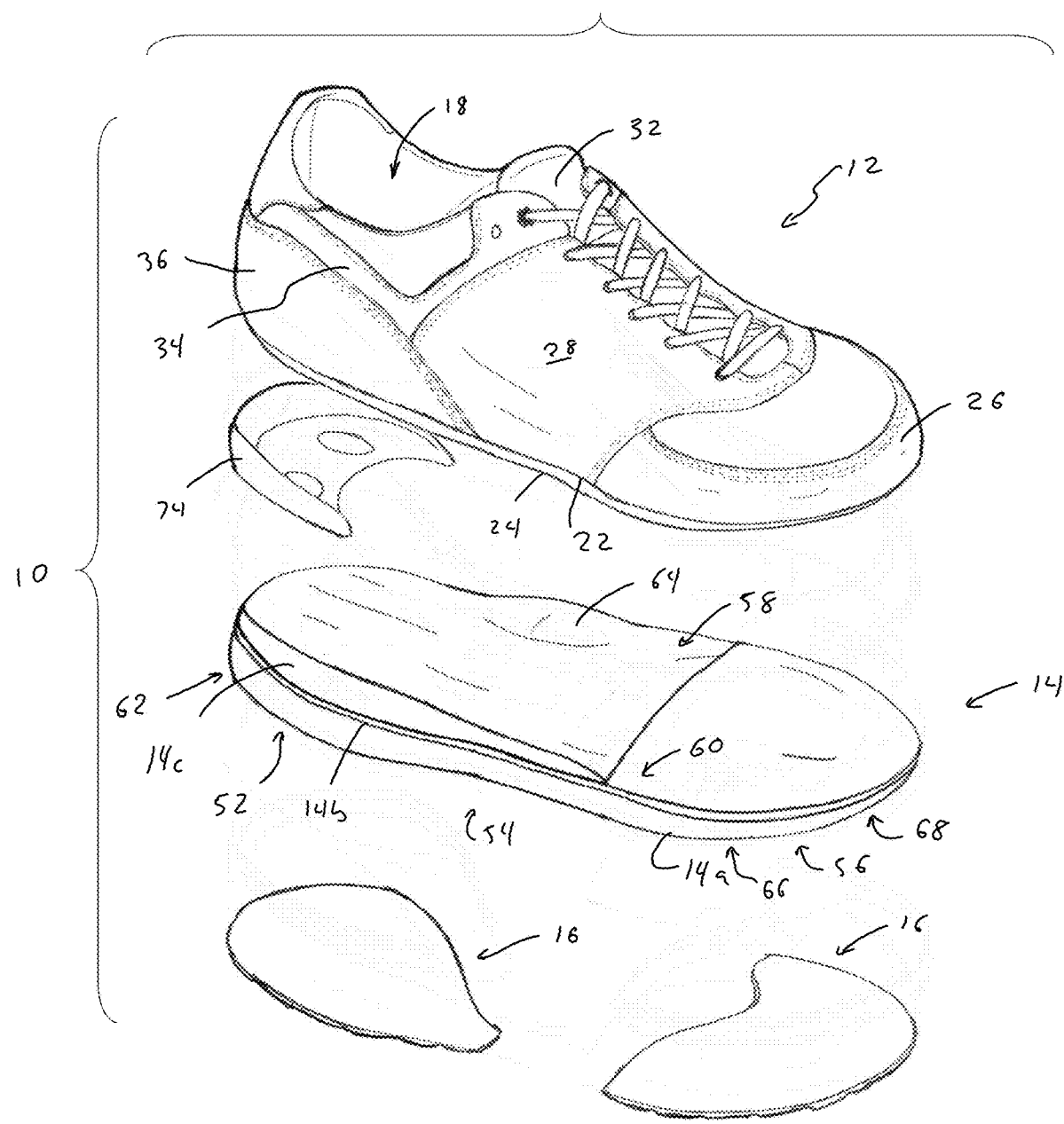
FIG. 2 is a front perspective exploded view of the sneaker.

As can be seen in FIG. 2, the interior 18 of the upper 12 is generally enclosed at the lower portion thereof by a lasting board 24 to which the upper 12 is affixed around or adjacent a lower perimeter 22 of the upper 12 (depending on the particular construction method, as discussed further below).

The lasting board 24 and/or the portions of upper 12 adjacent perimeter 22 are, in turn affixed with midsole 14 with the lasting board 24 being positioned above the midsole 14. An insole 24 (FIG. 3) may be placed within the interior 18 above the lasting board 24. The insole 20 may be at least somewhat cushioned to provide additional comfort to the user and to cover the stitching used to attach the lasting board 24 around the perimeter 22. In one aspect, the insole 20 may also include or be completely of a resilin material, as described herein and exhibiting the desired energy absorption and/or tactile qualities. This may be done by fabricating the insole 20 entirely from the resilin material or by covering a resilin cushioning layer with a thin layer of fabric, leather, mycelium material, or the like such that the resilin material provides a cushioning layer for the insole 20. Still further, the insole 20 may be of a coated resilin material, according to various examples discussed below.

As can be seen in FIGS. 1 and 2, the presently described sneaker 10 is exemplary of a sneaker, particularly the upper 12, manufactured using a "cut and sew" process by which the upper 12 is fabricated from a number of individual sections of stock material corresponding with various portions of the upper 12. In particular, the individual sections are cut from the stock material in flat, two-dimensional shapes, as needed as dictated by the desired final form of the upper 12, and are sewn together along various seams that at least partially give the upper 12 its desired three-dimensional form. Such sewing may be augmented by the use of various adhesives along the seams and may be carried in whole or in part over a last that corresponds with the desired shape of the interior 18 of upper 12. In particular, the lasting board 24 is typically sewn to upper 12 over a last and, with respect to typical construction of the depicted athletic sneaker 10, and similar footwear, completed using a "Strobel" stitch using specialized machinery that joins the material portions of the upper 12 that define the perimeter 22 with lasting board 24 in an abutting edge-to-edge seam. The resulting "Strobel sock" including the assembled upper 12 and lasting board 24 is then affixed with the midsole 14, which is most often done using adhesive or the like. In some forms of construction, the affixation between the lasting board 24 and the midsole 14 can be augmented or completed using stitching, such as Blake stitching or the like, or using stitches along particular areas of the upper 12 associated with features attached to the midsole 14, as discussed further below.

As can be appreciated, the pieces and sections of upper 12 may generally correspond with particular areas of the upper 12 but may vary according to their particular shape and placement depending on the desired stylistic appearance of the sneaker 10, as well as the desired fit, flexibility, and support of the athletic sneaker 10 (which may be influenced or dictated by the intended use of the athletic sneaker). In the exemplary depiction of FIGS. 1 and 2, the various portions of the upper 12 may include a toe tip 26, and a vamp 28 extending from the toe tip 26 upward to the throat 30 of the athletic sneaker 10. A tongue 32 extends upwardly along the throat 30 from vamp 28, and opposite quarters 34 extend rearwardly from the toe tip 26, to define the portions of lower perimeter 22 along the respective sides of upper 20, and downwardly away from the throat 30. A heel counter 36 extends around the rear of the upper to connect between the two quarters 34a,34b around the heel of the wearer. Further, medial and lateral collar portions 38 can extend upwardly from heel counter 36 and rearwardly from the respective medial and lateral quarters 34 to define respective portions of the topline 40 of the upper 12. A heel tab 42 is positioned above the heel counter and connects between the rearward-most ends of the respective collars 38 to define the rear section of the topline 40. An inner liner 44 (FIG. 3) can extend through all or part of the upper 12 to define the interior 18 thereof and can be affixed with the individual outer portions of the upper 12 along which it extends.

In a similar manner the outer, including the presently-depicted midsole 14 and outsole 16 can include a number of different regions that may be defined relative to one another to varying degrees or by varying characteristics. Most notably, the outer (midsole 14 and outsole 16) can be structured and defined by the portions of the foot that it supports relative to the ground and the manner by which such support is achieved. In this respect, both the midsole 14 and outer 16, where applicable, can be discussed in terms of corresponding heel (or rear-foot) 52 portions, mid-foot 54, and fore-foot 56 portions, as well as medial 58 and lateral 60 portions. In various contexts, combinations of such portions can be used to refer with greater or lesser specificity to the portions of the outer, for example, by reference to the medial, 58 heel 52, or the like. Still further, various specific portions within the various regions may be of specific relevance and, accordingly, given specific designations, including the heel-strike 62, the arch 64, the metatarsal head area 66 (i.e. beneath the balls of the feet), and the toe spring 68. Both the midsole 14 and the outsole 16 can be of varying materials, shapes, constructions, etc. within and among these regions, sub-regions, or specific areas to provide the desired fit, cushioning, stability, traction, and aesthetic qualities of the particular type or specific implementation of an article of footwear, such as the depicted sneaker 10, as well as to achieve any desired weight characteristics of the sneaker 10, various examples of which are discussed below.

In general, the midsole 14 can be particularly structured to anatomically correspond with the sole of a wearer's foot (or a range of wearers' feet according to known schemes for sizing sneakers and the like). Such structuring may include constructing midsole 14 with a greater thickness in the heel 52 portion and a comparatively lower thickness in the fore-foot 56, which can provide increased material cushioning for the heel 52, as the heel 52 typically makes first contact with the ground during a normal stride with a forward-leaning foot position and reduced material under the fore-foot 56 for weight-saving purposes, as less cushioning is needed under the fore-foot of the wearer. Still further, the heel strike 62 portion may be shaped or otherwise structured to increase cushioning even further in such a high-impact area, as well as to promote forward-rolling of the foot to smoothly bring the fore-foot 56 into contact with the ground. In a similar manner, the toe spring 68 can be upturned or otherwise structured to reduce effort in push-off by the wearer, such as during running or walking.

Figure 3:
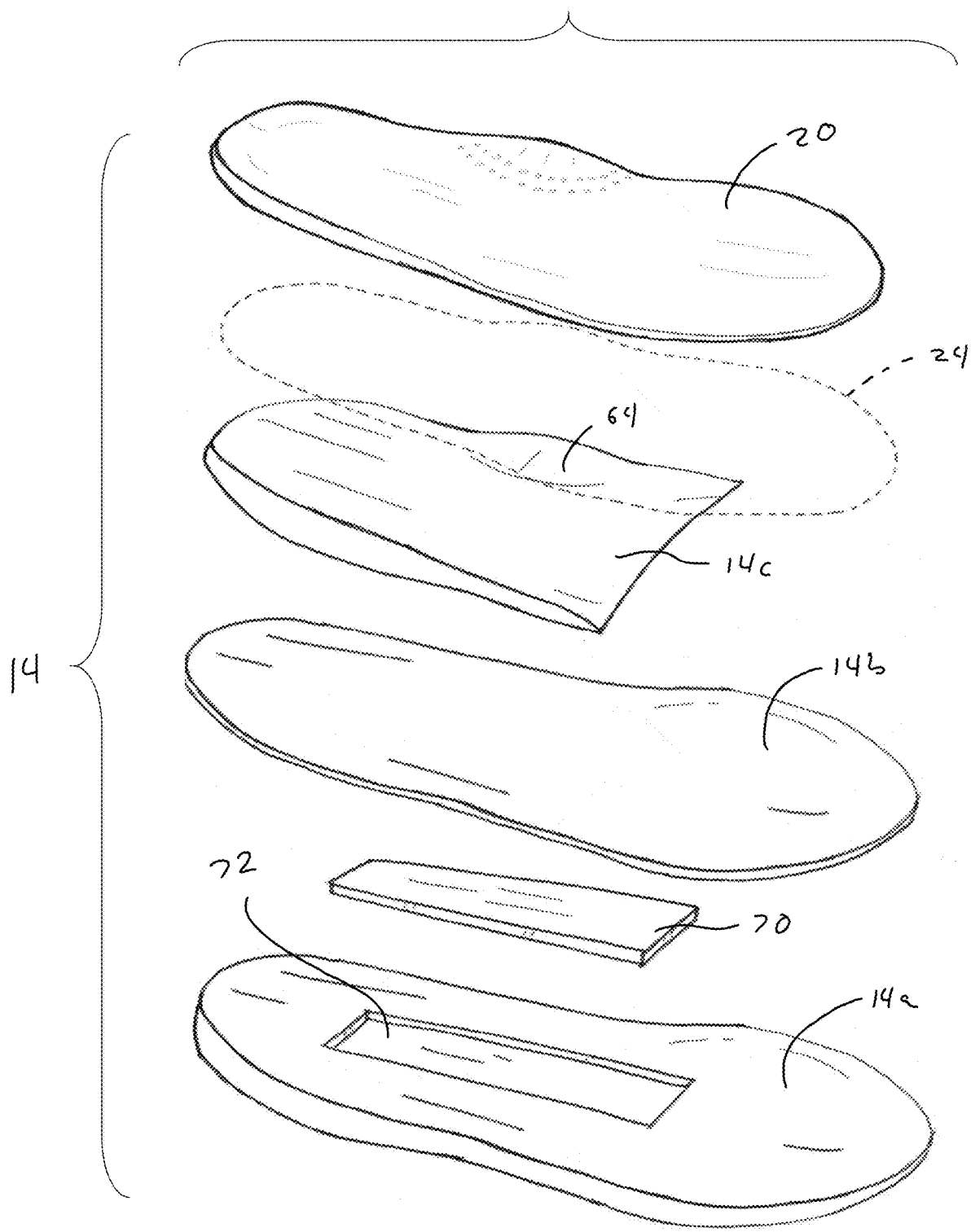
FIG. 3 is a front perspective exploded view of an midsole of the sneaker.

Within the mid-foot 54, the midsole 14 can be structured to provide reduced weight by removing material in areas where the foot does not normally contact the ground. In this manner, the midsole 14 can be structured to extend upwardly relative to the heel 52 and fore-foot 56 areas, at least on the medial side 58 thereof, with the midsole 14 remaining close to the ground plane within the lateral side 60 in some applications. The outsole 16 can be structured to correspond with such midsole 14 construction, including by eliminating material within the medial 58 mid-foot 54 or by being formed in separate heel and forefoot portions with no portion of outsole 16 being positioned along the mid-foot 54, as shown in FIG. 3. As discussed further herein, the outsole 16 can be further structured, including by incorporation of different materials as well as within other portions thereof corresponding to the various regions and areas discussed above. The midsole 14 can be further structured within the mid-foot 54 such that the arch 64 extends upwardly to provide support for the arch of the wearer to relieve muscle strain during heel-to-toe rolling of the foot and during push-off in particular. In this respect, the midsole 14 may not fully extend upwardly through the entire arch of the wearer (i.e., along the side of the foot), with portions of the upper 12 and the insole 20 (and/or specific inserts) providing additional support for the arch of the foot extending upwardly and medially from the midsole 14.

As shown in the exploded view of FIG. 3, midsole 14 can be fabricated from a number of different pieces of the resilin material using selected ones of the resilin compositions described above, to achieve an implementation of the above-described structure. In the illustrated example, a lower midsole 14a can extend over the entire length of the sneaker 10, including through the heel 52, mid-foot 54, and fore-foot 56. An intermediate midsole 14b can, similarly, extend over the entire lower midsole 14a and can provide different properties with respect to cushioning or appearance to contrast with lower midsole 14a. The combined lower midsole 14a and intermediate midsole 14b can provide at least the desired cushioning and positioning for fore-foot 66. A heel wedge 14c can be positioned over intermediate midsole 14b and can extend generally through the heel 52 portion of the midsole 14. In this respect, the heel wedge 14c can be tapered to a thin edge within the mid-foot 54 or fore-foot 56 portions to provide a smooth transition to the intermediate midsole 14b. Further, the heel wedge 14c can be structured to extend upward along at least the medial 58 portion of the mid-foot 56 to provide the desired support for at least a portion of the arch 64. In this respect the heel wedge 14c can be asymmetrical to extend farther into the mid-foot 56 along the medial 58 side to correspond with the positioning of arch 64, as well as the general asymmetry of the foot.

As can be appreciated, the midsole 14 construction depicted in FIGS. 1-3 is similar to what may be referred to as a "retro" style sneaker 10, wherein midsole 14 is constructed by a "cut-and-buff" process in which large sheets of bulk polymer foam, such as EVA, are cut into the desired shapes for lower midsole 14a, intermediate midsole 14b, and heel wedge 14c, which are then cemented together using suitable adhesive. Exposed edges, as well as the toe spring and heel kick areas, of the resulting assembly are then "buffed" using an abrasive material on appropriate machinery to form a consistent outer edge in the desired final shape. In this manner, the separate pieces 14a,14b,14c of the midsole 14 appear as a cohesive unit, while utilizing the laminated structure to achieve the desired shape profile and cushioning characteristics.

The presently-described resilin material can be used in various implementations to achieve a midsole of the depicted retro style. In one example, the resilin material can be formed, particularly by the above-described cross-linking and solvent exchange steps, in sheets corresponding to the desired maximum thicknesses for the lower midsole 14a, intermediate midsole 14b, and heel wedge 14c (noting that in some instances, the lower midsole 14a and the heel wedge 14c may be of the same stock sheet). Additionally, as it is typical to use various foams (e.g., EVA foam) in one or all portions of a shoe midsole 14, the resilin material used for the present midsole 14 (or at least one of the resilin materials in examples where different materials are used for the various portions 14a,14b,14c of the midsole 14) can be a foamed resilin material, as discussed in general above. The desired lower midsole 14a, and intermediate midsole 14b can be cut into the desired profile (depending on the size, style, and overall desired configuration) of midsole 14, and the heel wedge 14c can be cut in both the desired profile (i.e. matching the profile of lower and intermediate midsoles 14a,14b within the heel area 52) and angled wedge shape.

In the alternative, the individual pieces 14a,14b,14c can be directly molded into the above-described shapes, such that additional cutting or shaping is not needed such that the appearance of a cut-and-buff midsole is achieved without the wasted material from the actual process. In one example, such molding can be achieved, as discussed above, by providing molds with cavities corresponding to the desired shapes for the midsole pieces 14a,14b,14c and filling such cavities with a purified and denatured recombinant resilin composition, as discussed above, with a cross-linking solution of the various types discussed above such that the resilin protein cross-links in the mold. In this respect, the masses of cross-linked resilin material will generally retain the shape derived by the mold cavity. One of the various nonaqueous solvents can be exchanged for the solvent originally present in the resilin material mass to achieve the desired composition for the midsole pieces 14a,14b,14c. It is noted that the solvent exchange process may result in some shrinking of the molded resilin material pieces (e.g., 14a,14b,14c), which may be in the range of between 10% and 40% and in one embodiment about 25% of the pre-exchanged resilin material volume. In this respect, the molding step may be carried out to account for a determined or predicted level of shrinking, including by appropriately adjusting the size and configuration of the corresponding mold cavity.

In various implementations of either of the above-described fabrication processes for midsole 14, different recombinant resilins or different mixtures of different recombinant resilin compounds, as well as different cross-linking solutions and different nonaqueous solvents can be used to achieve different midsole pieces 14a,14b,14c with different properties determined to be desirable for its overall incorporation into midsole 14. In one respect, the composition of lower midsole 14a can be selected to provide a desired level of energy return and/or resilience, while heel wedge 14c and/or intermediate midsole 14b can be selected to provide a desired level of cushioning. Additionally or alternatively, the particular characteristics of foamed resilin can be specifically derived or controlled to achieve additional characteristics advantageous to the various portions 14a,14b,14c of midsole 14 and/or of midsole 14 as a whole. In one aspect, the introduction of bubbles to derive a foamed resilin material can reduce the specific gravity of the material and can, accordingly, be used, subject to other requirements or desired characteristics of midsole 14 to reduce the weight thereof by, effectively, reducing the overall amount of material. Additionally, the introduction of distributed air bubbles throughout a matrix of resilin material can alter the material properties of the overall solid beyond the simple reduction in specific gravity. In one aspect, the presence of air bubbles can change the response of the midsole 14 to the application of compressive loads due to the foamed solid exhibiting a two-stage compressive durometer response. In this respect, the foamed solid resilin material can exhibit a first compressive durometer response as the air bubbles collapse under load, such response being dictated by the rate at which air exits the voids and from the foam solid overall (in the case of open-cell foam, which results from the above-described step of air bubble introduction). A second response is presented once all or a significant number of the cells are collapsed such that the mass becomes more solid and exhibits an increased durometer more comparable to that of the material itself, without the presence of voids.

In various examples, the different methods for introducing air bubbles, as well as the use of different types and quantities of additives, specific crosslinking processes or agents, and the like, can result in foams having varying cell sizes and, accordingly different properties of the resulting foamed resilin solid. In one example, fumed silica, as a thickening agent, and sodium bicarbonate, as a chemical blowing agent, can be added to the resilin before crosslinking. These additives can facilitate uniform distribution of air bubbles during the introduction process, resulting in more uniform cell distribution in the finished foamed resilin solid. Altering the amount of the fumed silica and/or sodium bicarbonate can allow for one mode of control for the average bubble size within the resilin material and can promote even distribution of such air bubbles.

In one implementation, midsole 14 can include at least one portion (including portions 14a, 14b, and 14c) of a solid resilin foam prepared by dissolving the purified recombinant resilin material in PBS at a pH of about 7.4. Sodium bicarbonate can be added to the resilin solution as a chemical blowing agent, which may be done in combination with fumed silica, as a thickening agent in varying amounts, to control the size and distribution of air bubbles, as discussed above. In various examples, between 6 mg/mL and 20 mg/mL of sodium bicarbonate (or between 0.2% and 2% by weight) can be added to the resilin solution. In general, sodium bicarbonate may be added at a maximum amount of about 33 mg/mL to prevent the sodium bicarbonate from inhibiting gelation. The further addition of fumed silica (or other thickening agent) in quantities ranging between 4% and 10% by weight may result in a resilin solid (i.e., after the subsequent processing steps with the addition of further components as discussed below) with generally evenly-distributed bubbles. In specific implementations, the addition of fumed silica in relatively low amounts, including between 4% and 5% by weight, result in relatively large bubbles, in the range of about 0.2 mm to 2 mm, within the resulting resilin material. Adding fumed silica in an amount greater than 5% by weight (including in an amount of up to about 10% by weight) may result in a foamed resilin with relatively smaller bubbles (and increased overall density), including bubbles in the range of 0.05 mm to 0.2 mm.

A solution of ammonium persulfate in a concentration of between 100 mM and 225 mM can be added to the purified and thickened resilin. Xanthan gum may also be used in combination with the ammonium persulfate solution to further increase the viscosity over the thickening agent to further aide in trapping bubbles within the solution. In various specific implementations, ammonium persulfate can be added in amounts between about 10% and 20% by weight and, more specifically in amounts between 13% and 16% by weight. In such implementations, xanthan gum can be added in amounts between 1% and 2%. A crosslinking catalyst can be added before or after addition of the foaming agent and can be selected to be activated by one of heat or light. In one example ruthenium (II), which is activated by white light, can be used in amounts between 10% and 20% by weight (other catalysts can be used as an alternative, according to the examples discussed above). After addition of the catalyst and foaming agent, the solution can be vortexed to allow bubbles to develop within the resilin material. In one example, vortexing can be carried out for 3.5 hours at a temperature of about 80° F. After the solution is vortexed, it can be appropriately crosslinked (e.g., using heat or light) and can be subjected to a solvent-exchange process, as discussed above, including using propylene glycol in an example. Examples of foamed resilin material solids S1 and S2 with open cells C1 and C2 or relatively smaller and relatively larger sizes, respectively, dispersed in a resilin matrix M1 and M2 are shown in FIG. 4.

In additional or alternative implementations, a syringe pump can be used to introduce dissolved nitrogen, while crosslinking the resilin, as either a primary source of air bubbles within the resilin material, or a supplement to air bubble generated using an agent, as discussed above. In one implementation, an ammonium persulfate solution (e.g. of either 225 or 550 mM) can be added to a solution of resilin in PBS (e.g. of about 27% by weight of resilin). The resulting solution can then be centrifuged (e.g. for about 5 min at about 7200 rcf) and added to a syringe pump. The pump can then be purged with nitrogen gas (e.g. for about 3 minutes) and then sealed. The pump can then be set to either 500 psi or 1600 psi and heated (e.g. for between about 2 hours and about 6 hours at about 83° C.). After releasing the pressure, the resilin can be heated for an additional interval (e.g. for between about 1 hour and about 2 hours at about 83° C.) It is noted that crosslinking at these pressures may proceed at a slower rate than crosslinking at atmospheric pressure, likely due to the increased amounts of dissolved oxygen. The addition of a thickener, as discussed above may further enable uniform foams via such a process. The various foamed resilin materials can also be used in the additional products discussed above, including in cores for golf balls, softballs, or the like, handles or grips, e.g., for sports equipment such as golf clubs or tennis rackets, as bicycle grips or motorcycle grips, or as grips for tools and industrial uses such as hammers, nail guns, jackhammers, etc. In further embodiments, the foamed resilin materials provided herein can be used in safety and protective gear, such as padding for protective equipment such as helmets, elbow or knee pads, shoulder pads, protective gloves, or hard hats.

The separate pieces 14a,14b,14c of midsole 14, derived by any of the processes discussed above, including those that result in a foamed resilin material having cells of varying sizes and corresponding densities, can then be laminated together using appropriate adhesives, adhesion of which with the present resilin material being, in some instances, augmented by the prior application of a primer material, such as acetone or a similar material. In the alternative, it may be possible to affix together multiple pieces of the present resilin material using an additional cross-linking step prior to solvent exchange, wherein a layer of the cross-linking solution is applied between pieces, such as the midsole pieces 14a,14b,14c of resilin material, which are then retained in contact with each other. The addition of heat and/or light (depending on the particular cross-linking solution) can help achieve the desired cross-linking of the proteins along the contact area between such pieces. After such cross-linking, the pieces 14a,14b,14c are joined together and the solvent exchange step can be carried out.

In a still-further variation of the above molding process, it may be possible to add different purified and denatured recombinant resilin compositions into a single mold in layers corresponding with different portions of midsole 14, including the pieces 14a,14b,14c illustrated in the present example and to apply a single cross-linking solution to the layered materials to obtain a single midsole 14 having multiple different types of resilin material in layers or other portions therein, which can then be subjected to solvent exchange to obtain a midsole 14 having different properties in different areas thereof, including in the illustrated layers.

Such a process may be used to obtain other variations of material in connection with different midsole 14 types discussed below.

In some examples, the depicted layered structure can include layers 14a,14b,14c having different configurations and corresponding properties according to the above descriptions. In particular, the different layers 14a,14b,14c can be of foamed resilin materials having different cell sizes and/or densities. In one example, the outermost layer 14a can be of a higher density configured for protection and energy return with at least the middle layer 14b having a lower density for cushioning. Other arrangements, including various combinations of foamed and non-foamed resilin material can be implemented according to the desired characteristics of the midsole 14. As can be appreciated, a foamed resilin material according to the above description can also be used for all or a part of insole 20 (FIG. 3) and for various padding or the like in upper 12 (including within collar 38 and tongue 32).

In additional examples, the general effects (reduced specific gravity, two-stage durometer response, etc.) of a foamed resilin material can be achieved by removing material from solid resilin material layers prior to laminating, or adhering, them together. In one example several sheets (including more than the three depicted layers 14a,14b,14c) can be made in various thicknesses, including in one example thicknesses of between about 1 mm and 5 mm. The sheets can be cut in various patterns to remove material with a mismatch in the patterns among the various layers to mimic the distribution of cells in a foamed material after lamination. In various examples, the sheets can be cut using a die, water jet, lasers, etc. in either stocked patterns or in the desired shape of midsole 14. In the latter example, the patterns can be varied and scaled according to the midsole size or configuration, which can be done to ensure that no holes intersect the edge of the midsole 14 and/or to achieve a midsole 14 with varying density characteristics in the various regions thereof. Additionally, a solid layer can be provided as the outermost layer to provide a closed, smooth outer surface for midsole 14, including for adhesion with outsole 16. The layers can be adhered together or can be re-crosslinked after arrangement in the desired configuration. Still further, the layers can be sublayers, such that they can be arranged in different overall layers, such as the depicted layers 14a,14b,14c having different properties.

Figure 6:
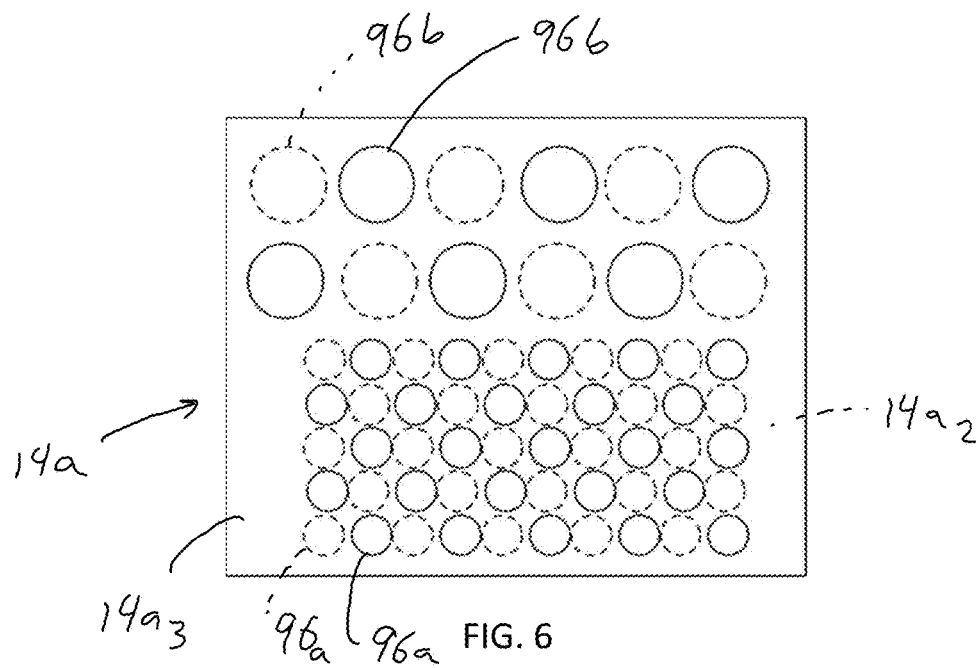
FIG. 6 is a top elevation view of a further example of a laminated perforated structure of solid resilin material.
Figure 7A:
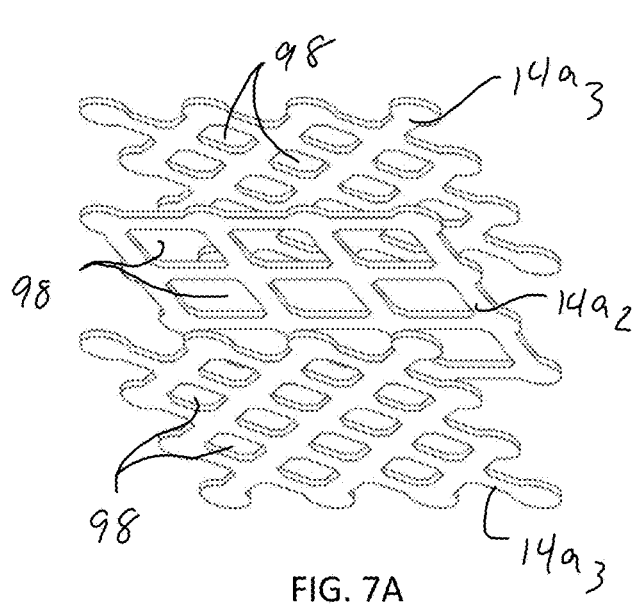
FIGS. 7A and 7B are exploded perspective and top elevation views of a further example a laminated perforated structure of solid resilin material.
Figure 7B:
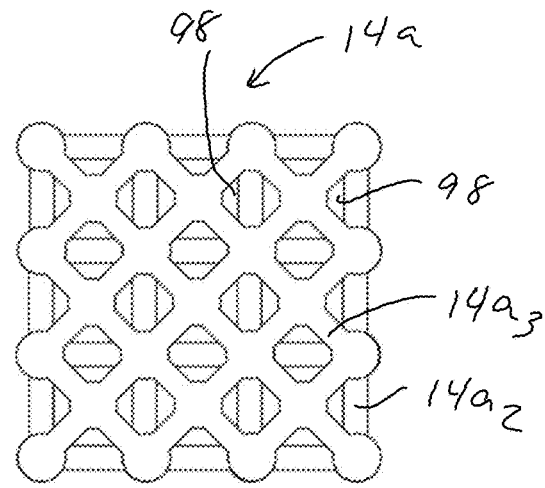

One example, of a layered structure is shown in FIGS. 5A and 5B, wherein three sublayers $14a_1$, $14a_2$, and $14a_3$ are shown having holes, or perforations 96, therein. As shown, in FIG. 5A, the outermost sublayers $14a_1$ and $14a_3$ have perforations 96 that are offset from the perforations 96 in the middle sublayer $14a_2$. As shown in FIG. 5B, when the sublayers $14a_1,14a_2,14a_3$ are stacked, the perforations 96 in the outer sublayers $14a_1$ and $14a_3$ align with each other in an offset manner from the perforations 96 in the middle sublayer $14a_2$. The depicted pattern can be repeated in additional sublayers to provide a midsole layer, such as layer 14a of the desired thickness. In a further example, an entire midsole 14 can be of such a construction. As shown in FIG. 6, the perforations can vary in size including between regions of the midsole. In one implementations, the relatively smaller perforations 96a can be positioned to provide a denser portion of the midsole 14 that can, for example, be positioned in the arch area 64 of midsole 14. The relatively larger perforations 96b can be positioned to provide a relatively softer portion of the midsole 14 that can, for example, be positioned in the heel strike area 62 of the midsole 14. Other examples and arrangements are possible according to known midsole constructions and the additional examples provided herein. In a further example shown in FIGS. 7A and 7B, holes in various geometric shapes other than circles or standard perforations can be used. Such shapes can be irregular or uniform and/or can vary with different regions of the midsole 14 and may, in some implementations be derived to result in a so-called macro-structure based on the various arrangements of openings 98 among layers $14a_1,14a_2,14a_3$ (FIG. 7A) when laminated together (FIG. 7B). Such structures can exhibit asymmetric properties during loading, including an asymmetric, or inversed, Poisson's ratio during loading or when subject to stress such that certain portions may contract in one direction (i.e. along X, Y, or Z axes) when loaded (i.e. in another of the X, Y, or Z axes) or may otherwise increase in durometer in response to loads. Such properties, in some implementations, can be tuned to the needs of the specific midsole 14 and/or specific areas thereof.

Continuing with respect to FIG. 3, the above-described layered structure for midsole 14 can also provide for the incorporation of an internal shank 70 therein. In general, shanks, such as the depicted, substantially flat "credit card" shank 70, help to provide structural rigidity to a midsole 14 through the mid-foot 54, where the wearer's foot exhibits some flexibility (i.e., more than in the heel 52) such that many potential wearers experience strain or fatigue within the plantar muscles of the foot and the adjacent soft tissue through repeated loading and unloading within the mid-foot 54, such as during running or rapid changes in lateral direction. In this respect, the rigidity provided by the shank 70 localizes flexing of midsole 14 to within the fore-foot 56, where the joints of the foot are most flexible, while also maintaining the insole 20 in more consistent contact with the wearer's foot through the mid-foot area 54 to reduce muscle strain and provide increased support for the foot within the arch 64. In the illustrated example, the shank 70 is of a generally flat piece of material (that may be ribbed or otherwise shaped to increase rigidity while maintaining an overall flat character) with high stiffness and high elastic deformation such as various plastics, carbon fiber reinforced polymer ("CFRP"), Kevlar® reinforced polymer, steel (such as spring steel), or the like. Such a shank 70 can be laminated between the layers 14a,14b,14c of the midsole 14, including between the lower midsole 14a and the intermediate midsole 14b, as illustrated. As further shown, the shank 70 can be inserted in a cavity 72 formed in lower midsole 14a, such as by additional processing of a cut resilin sheet (e.g., grinding or machining) or during the above-described molding process.

The above-described midsole 14, fabricated according to any of the various examples discussed above and further variations that would be understood based on the description and depiction of the midsole in FIGS. 1-3, can be bonded with outsole 16, including using various cements or adhesives used for such purposes in connection with midsoles 14 of a typical foam construction. In some examples, the surface of midsole 14 (at least in areas where outsole 16 is present) may be treated with a primer material prior to application of the selected cement or adhesive to improve bonding, depending on the particular composition of the resilin material of midsole 14. Solvent-based adhesives (also referred to as cements) have been used for such purposes, including in affixing midsole 14 to upper 12, and are generally accepted as having a relatively low cost and rapid fixing times and high workability. Such solvent-based adhesives and cements can be used with parts or portions of the sneaker 10 of the present resilin material in the same way that they can be used with elastomers, including to affix outsole 16 to midsole 14 and to affix midsole 14 to upper 12, as well as to attach together various portions of midsole 14 formed of different pieces of resilin material. More particularly, such adhesives can be used to affix the outsole 16 to the midsole 14 or to affix additional elements with upper 12, including the depicted heel stabilizer 62, which is fixed between the rear portions of both the upper 12 and lasting board 24 and the midsole 14.

In some circumstances, ultraviolet ("UV") light curing or activated adhesives can be used to replace solvent-based adhesives in whole or in part. Such UV curing or UV activated adhesives can include acrylic-based cements or modified epoxy materials. In either case, the compound includes a photoinitiator that undergoes a chemical reaction when exposed to UV light, causing the release of byproducts to that reaction. Those byproducts interact with the remaining compound to cause hardening of the compound or to initiate the reaction that results in hardening. The incorporation of and reliance on the photoinitiator allows for the cement or adhesive to cure "on demand" rather than within a short interval from application (e.g. exposure to air in an acrylic cement or mixing in the case of an epoxy). This may allow for the various portions of upper 12 and/or midsole 14 to be coated with the adhesive with each such piece being activated when ready for affixing with the desired other piece or element. Various heat-activated adhesives can be used in a similar manner. In general, such adhesives can be made to set upon the application of heat above a certain threshold temperature or can use heat as a catalyst for curing (in the case of epoxy, for example). In one example, the heat-activated adhesive can be applied, as desired, with the assembled sneaker 10 being subsequently run through a heat tunnel to initiate or exacerbate the setting of the adhesive to result in the finished component or product. In some applications, the adhesives can exhibit relatively lower levels of adhesion in an initial state such that pieces or components can be assembled without stitching before heat is applied to set the heat-activated adhesive.

Still further, water-based adhesives and cements have been developed to act as a replacement for solvent-based compounds, as solvents frequently include volatile organic compounds ("VOCs") or other polluting chemicals (that may also be flammable). In one example, a polyurethane adhesive, for example, may have water as its primary "solvent" in that setting of the adhesive requires that the water evaporate from the compound. Accordingly, the application of heat may be used to speed or cause the adhesive to set. Additionally, pre-heating of the material to be affixed can also help speed the setting process. Water-based adhesives may provide certain characteristics that make them advantageous for the use in shoe fabrication, including fabrication of the present sneaker 10. Water based adhesives can exhibit reduced stiffening of the material and can be made of a relatively high viscosity to prevent absorption into the materials prior to setting, while still being sufficiently sprayable. Accordingly, in the same manner discussed above, water-based adhesives can be used to affix elements to upper 12 or to fix the upper 12 and lasting board 24 with the midsole 14.

As also mentioned above, the outsole 16 may be formed of one or more portions of rubber (including various synthetic rubbers and the like) selected for desirable characteristics, including density, abrasion resistance, bonding ability, and the like. In some implementations, the outsole 16 can also be of a resilin material that may be produced according to selected variations of the above-described process, to achieve desired density and abrasion resistance similar to what may be desired of rubber (including synthetic rubber). In such an example, the outsole 16 can be molded of resilin material, as discussed above, to achieve the desired ground-contact pattern, which may vary based on the intended use of sneaker 10. As discussed above, the outsole 16 may be applied over the entire outer surface 74 of midsole 14 (i.e., the surface closest to the ground). In a variation of the illustration in FIGS. 1-3, the outsole 16 may comprise a number of pieces of outsole material (including of varying characteristics) that can be affixed with midsole 14 in areas where contact with the ground is made and/or where grip or durability is desired.

Returning to FIGS. 1 and 2, opposite outsole 16, midsole 14 can be affixed with upper 12. As discussed above, such bonding may also be achieved using cement or adhesive, selected to achieve the desired bonding with upper 12 and midsole, one or both of which may be pre-treated with a primer or the like prior to cement or adhesive application. As illustrated, the upper 12 of the present example is of a Strobel construction, such that midsole 14 is primarily bonded to the lasting board 24, as well as the adjacent portions of the perimeter 22 of the exposed portion of upper 12 (defined around the various portions thereof discussed above). As shown, a heel stabilizer 74 can be assembled between midsole 14 and upper 12 along the perimeter of the heel 52 with portions thereof extending respectively upward and downward along adjacent portions of the midsole 14 and heel counter 36. Heel stabilizer 74 can add structure and protection in the area round the wearer's heel and can improve adhesion between midsole 14 and upper 12 around the heel 52 by being cemented with both upper 12 and midsole 14, both in the area directly between midsole 14 and upper 12, as well as along the side surfaces thereof in the areas contacted by stabilizer 74. In some implementations, the completed midsole 14 can be coated with a layer of finishing material, including polyurethane, Barge® cement or the like, or various corn or protein based materials, such as the corn-based prolamine protein zein, to encapsulate the midsole 14 and/or to provide a desirable visual or tactile quality for the portions of midsole 14 that may include otherwise exposed resilin material. In this respect, the coating may also improve bonding by way of an adhesive or cement such that an additional primer is not needed. In general, a suitable coating or finishing material has comparable elastic properties to that of the resilin material over which it is applied, to prevent separation or cracking of the coating.

Figure 8:
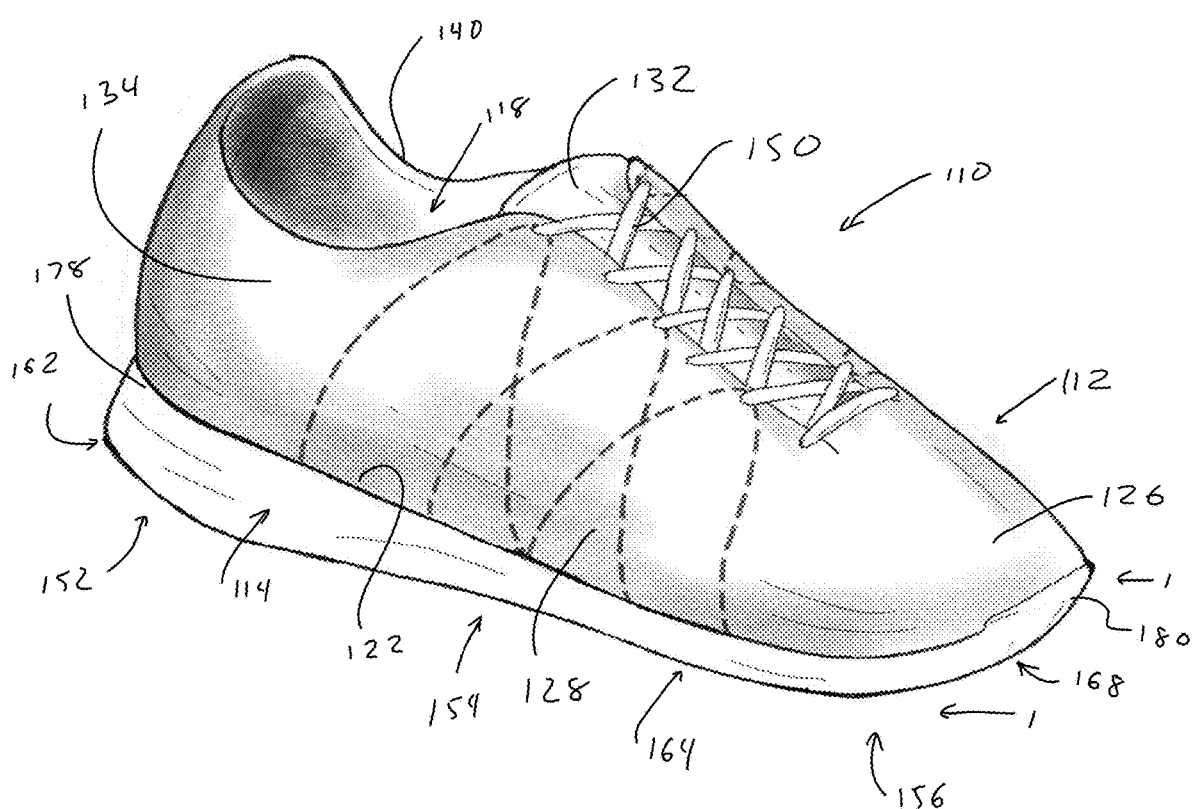
FIG. 8 is a front perspective view of a sneaker according to another aspect of the disclosure.
Figure 9:
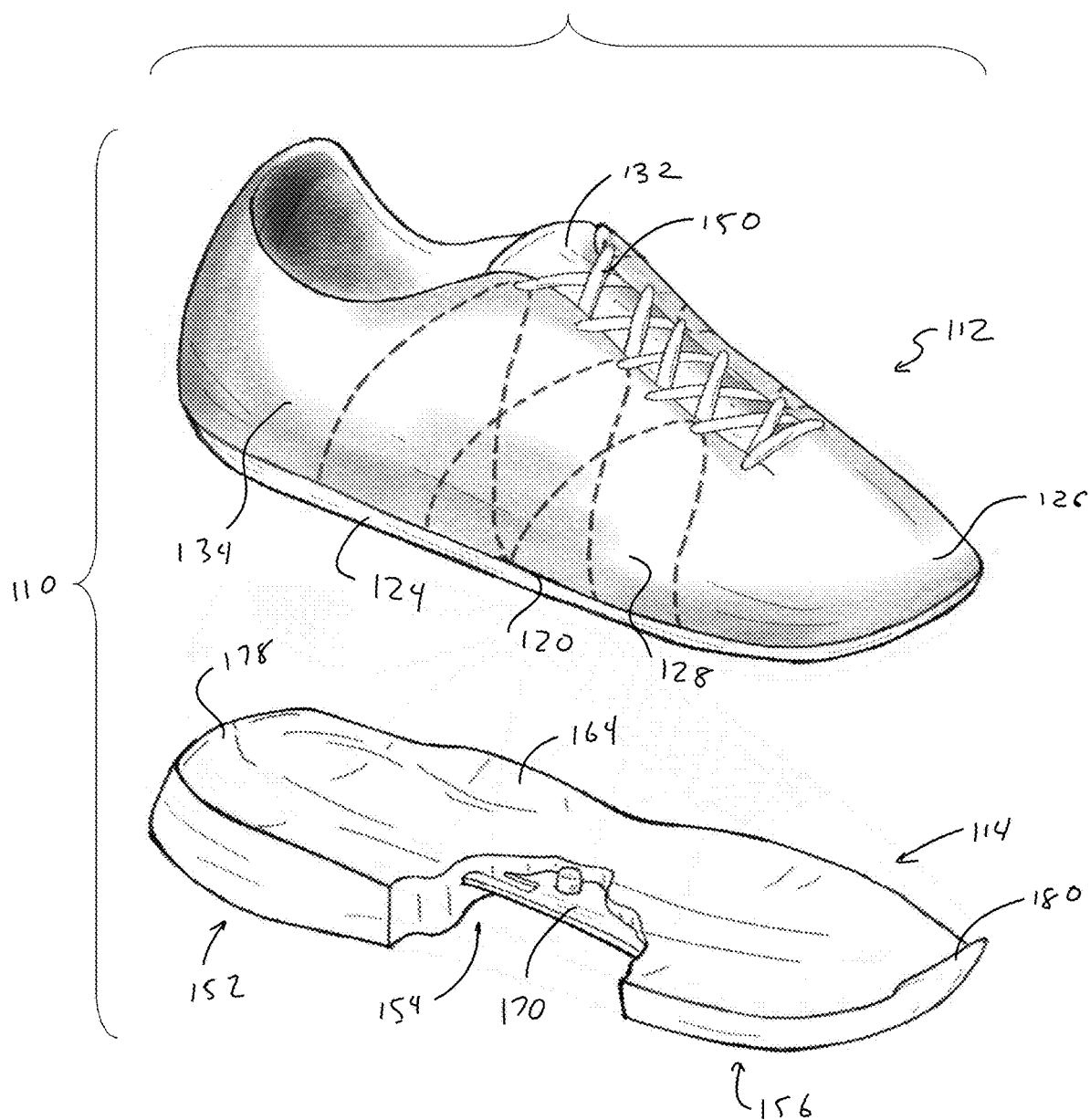
FIG. 9 is a front perspective exploded view of the sneaker.
Figure 10:
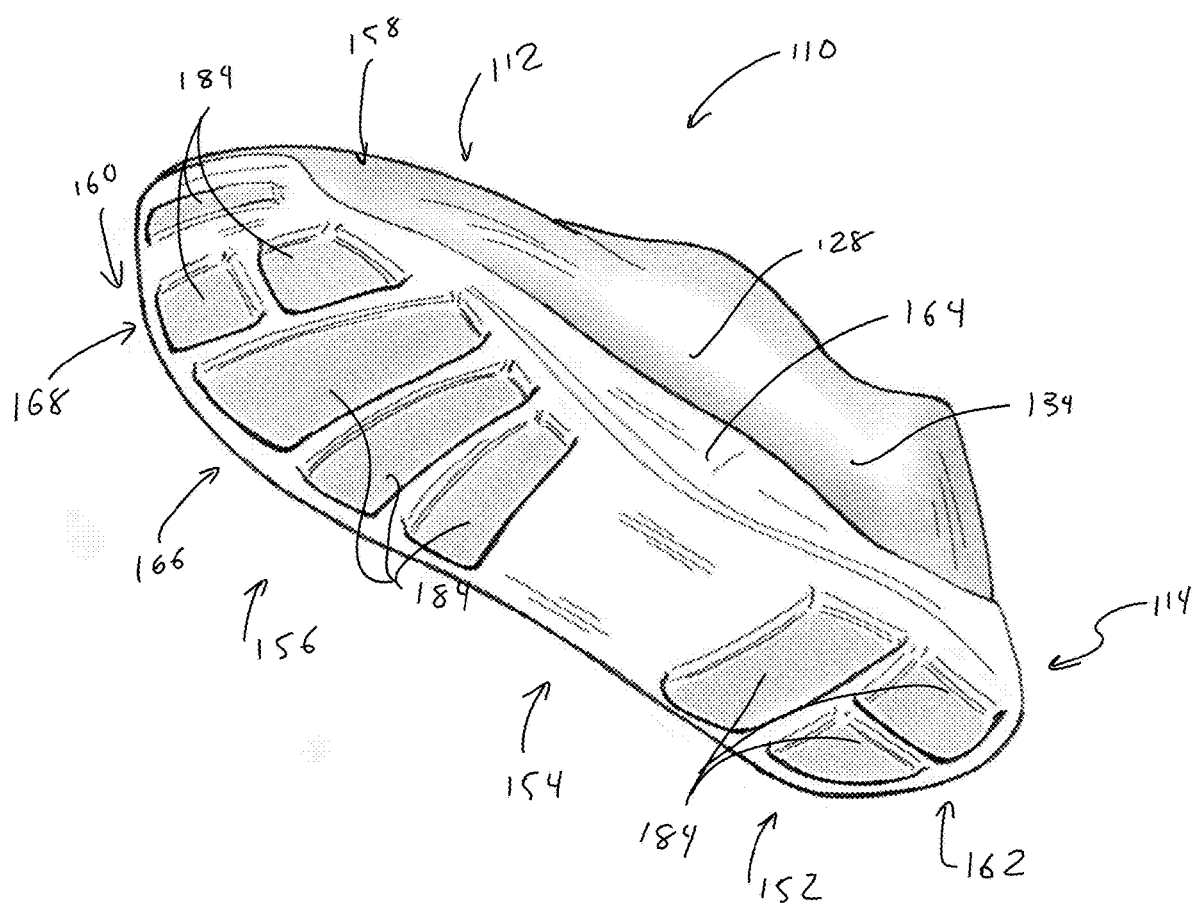
FIG. 10 is a bottom perspective view of the sneaker.

Turning to FIGS. 8-10, a variation of a lifestyle sneaker 110 is shown that incorporates stylistic and assembly characteristics developed previously for use in more performance-oriented footwear. In one aspect the upper used in connection with sneaker 110 can be a single piece or "seamless" upper or similar variations of the same. Such uppers can be of various woven or knit textile materials including various types of "technical" textile materials. Such textile materials can be of various natural or synthetic fibers and can be formed into the general shape of upper 112 using various 3-D knitting processes. Alternatively, upper 112 can be made of natural or synthetic leather, including in a non-seamless construction similar to that which is shown above in FIGS. 1-3.

Sneaker 110 can include an outer of or including a resilin material of a structure similar to or resembling those incorporating a molded elastomer foam. Such outers can include a midsole that is of a foam material, such as EVA or various composite materials including EVA or the like, which can be injected into a mold in an uncured state and allowed to cure in the mold to achieve the desired shape, which can include more organic or amorphous forms than possible with a traditional cut-and-buff midsole, such as that discussed above. Similarly, a thermoplastic foam, such as EVA can be cut into a stock form and compression molded under heat to achieve a similar effect. In some applications, a molded midsole may comprise a number of different foam materials, including in composition, density, etc., achieved by compression molding different pieces of foam, cut to mutually inter-engage, in a single mold or by injecting different foams into a mold simultaneously (e.g., dual-shot injection molding) or sequentially (insert molding). In a similar manner to that which is discussed above in connection with FIG. 3, the present resilin material can be molded of multiple materials, in processes similar to either of the above-described simultaneous or sequential molding processes to achieve a molded resilin midsole 114 having multiple materials of different characteristics for various purposes, including resilience, cushioning, wear-resistance, and the like, as discussed generally above and in the additional examples below. In various implementations, the illustrated midsole 114 can be of a foamed resilin material according to any of the above-described variations thereof, which can be configured according to the above description to achieve the desired properties of the material.

The illustrated molded resilin midsole 114 can include a contoured footbed 176. Still further, the variations in the shape of midsole 114 provided by molding can allow for adjustments in the shape of both the heel strike area 162, as well as the toe spring 168 to make midsole 114 suitable for various purposes. In the present example, the midsole 114 is illustrated as including both a heel wrap 178 and toe wrap 180 defined by respective portions of the midsole 114 that are relatively thin and extend upwardly by between about ⅛" and ½" to provide additional protection or traction along the portions of upper 112 adjacent to heel 152 and fore-foot 156, such as along heel counter 136 and toe tip 25. Additionally, the presence of heel wrap 178 and toe wrap 180 can provide additional area for adhesion between midsole 114 and upper 112 in areas that are often subjected to relatively large amounts of stress.

As also shown in FIG. 10, midsole 114 can include various molded-in features along the outer portion thereof (i.e. the ground-facing side opposite upper 112). Further, the outer of sneaker 110 may be configured such that midsole 114 contacts the ground along portions thereof during at least some use scenarios with no additional outsole 116 material present in such areas. In this manner, midsole 114 can be configured with various forms of treads 184 or other traction-generating features in the areas of midsole 114 not covered by a portion of outsole 116. In the particular example of FIG. 10, midsole 114 is shown with no additional outsole material thereon, such that the entire outer is comprised of midsole 114, which includes treads 184 distributed along the entire ground-contacting portion thereof such that an outsole is effectively defined on midsole 114. To achieve such a configuration in a useable manner, midsole 114 can be of a particular resilin material that is optimized for abrasion resistance (while maintaining acceptable levels of cushioning and/or rebound for the particular purpose for which sneaker 110 is intended), at least along the outer portions thereof and/or along the portion defining treads 184 (which can be in the general form shown or a variation thereof selected for various performance and stylistic considerations). In one non-limiting example, such a material may be achieved by adding fumed silica, or another aggregate or fiber having suitable properties, in an amount of up to about 20% by weight to the purified resilin material prior to cross-linking. The addition of fumed silica to the resilin material results in a material, after cross-linking, that has a higher abrasion resistance and a higher durometer (as discussed below). In an example, the resulting material can be used for only a portion (e.g. the ground-contacting portion or in an area that would otherwise comprise an outsole) of midsole 114, with the remaining portion of midsole 114 being formed of a more cushioning resilin material (i.e. without or with less fumed silica). Such a structure can be achieved, in one example, by separately forming the different portions of midsole 114 and bonding or cross-linking the materials together. In another example, a dual-shot or insert molding construction can be employed, as discussed further below. In a still further example, midsole 114 can be of a "functional gradient" construction in which a mold can be partially filled with purified resilin, which can then be extensively cross-linked to derive a first material. The mold can then be filled completely with additional cross-linking to a lesser degree than that of the first material. The resulting composite material could exhibit two different functional properties in the respective areas of different degrees of cross-linking. Notably, this process can be carried out with or without the above-mentioned aggregate material. In another example a solid resilin material of the same or different composition can be coated with an abrasion-resistant coating, including any of the above-described coatings.

In a similar manner to the implementation of midsole 14 discussed above, the midsole 114 illustrated in FIGS. 8-10 can incorporate a shank 170 (FIG. 9) to provide rigidity and support for midsole 114 in the manner discussed above. Midsole 114 can be adapted in one of a number of ways to securely receive shank 170 therein. In the illustrated example, midsole 114 can be molded over shank 170, which can be of a similar construction to the variations of shank 70 discussed above. In this manner, the mold used to form midsole 114 can be adapted to retain shank 170 therein prior to addition of the purified resilin protein prior to cross-linking, which can be achieved by including supports within mold that can support shank 170 in a suspended position within the mold cavity. In various examples, the posts can be integrated with the mold and any holes preset from removal of the posts from the molded midsole 114 can be filled with additional resilin material, including by the addition of more purified and denatured resilin protein, which can be cross-linked after filling of such holes. In another example, such holes can be filled with pre-fabricated plugs of resilin material, or the shank 170 can be supported on inserts prefabricated using a resilin material or other compatible foam such that the posts become integrated with midsole 114 during molding. In another example, shank 170 can be glued into a cavity in midsole 114 and can be covered by an insert of a resilin material sheet or other foam that can be glued over the shank 170. In another example, shank 170 can be insert molded with midsole 114 or adhered externally thereto along the outer surface thereof, in a manner similar to that which is described further below.

It will be appreciated that a midsole 114 of the present construction, including by formation of treads 184 along midsole 114 in place of a separate outsole, may be suited for the present embodiment of sneaker in the form of a lifestyle sneaker 110. In particular, the use of the presently-described molded resilin material for the ground-contacting portion of sneaker 110 and, therefore, primary source of traction, may result in sneaker 110 having a level of grip that is well-suited for everyday use, including walking and standing, while providing sufficient grip for needed intermediate light running or jogging, the ultimate amount of grip provided by midsole 114 may not be sufficient for use in athletic activities carried out on smooth surfaces (such as basketball), where quick changes in lateral direction are needed (such as tennis), or in other activities where additional underfoot protection may be desired (such as trail running). The potentially-reduced grip of midsole 114 may be offset, however, but gains in comfort by way of increased flexibility and lightness that midsole 114 imparts on sneaker 110 overall. In a similar manner, such gains in flexibility and lightness may also be advantageous for certain athletic activities, including running and jogging, such that a variation of sneaker 110 with a midsole 114 similar to that of the present embodiment may be adapted for use as a running sneaker. Such modifications may include the use of a resilin material with increased resilience or rebound, at least in the heel 152 area, or by the incorporation of small segments of outsole material in high-impact areas, such as in the heel strike 162 and toe spring 168 areas. In one example, the outer portions of midsole 114 (e.g. the lowermost, ground-contacting portion and visible sidewalls) can be of a solid resilin material to provide the desired abrasion resistance and traction, as well as to provide adequate support for any external features, while midsole 114 can have a core of a foamed resilin material. To achieve such construction, midsole 114 can be formed in separate interior and exterior portions that can be adhered or crosslinked together into a single midsole 114.

Figure 11:
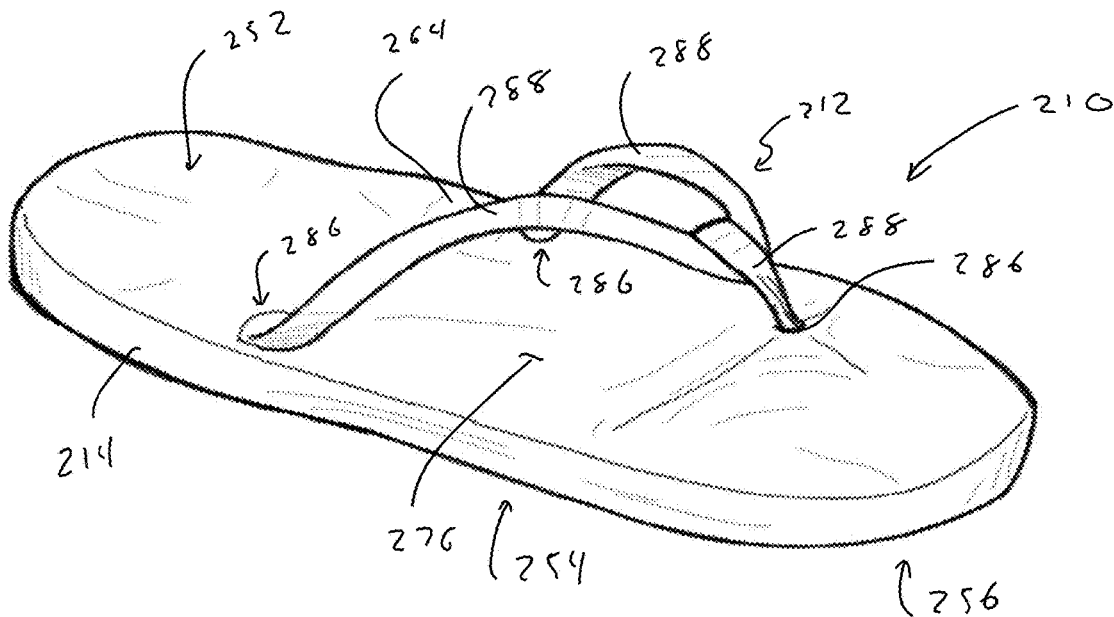
FIG. 11 is a front perspective view of a sandal according to an aspect of the disclosure.
Figure 12:
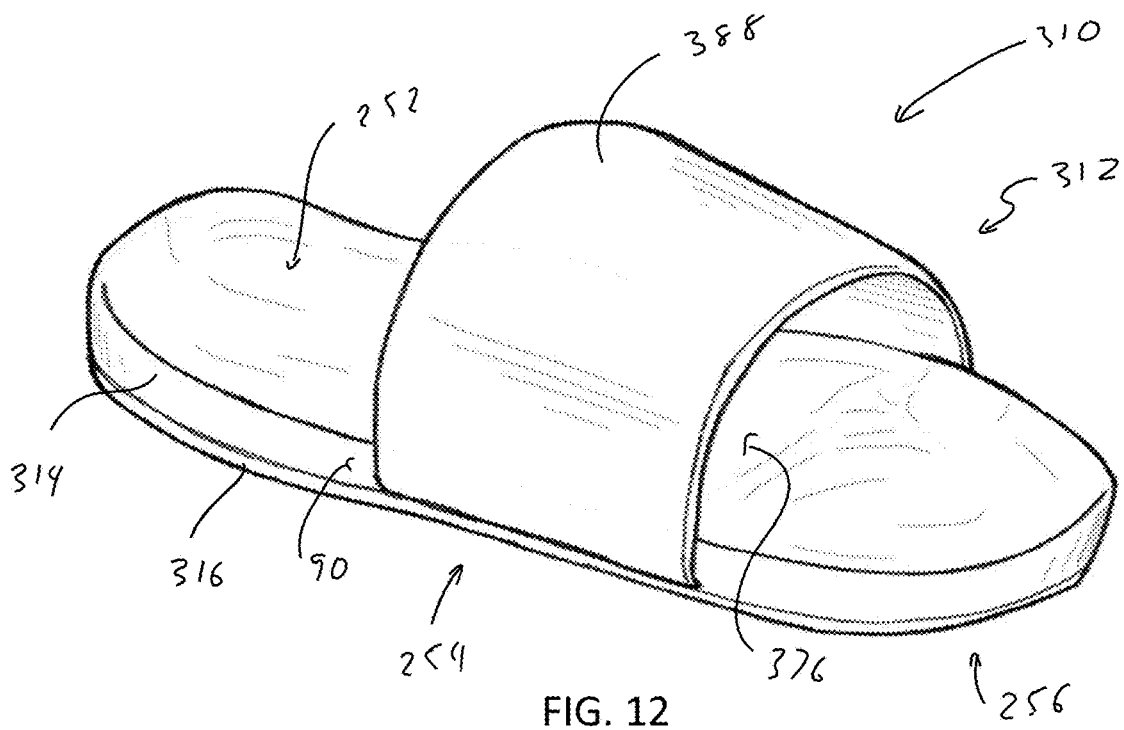
FIG. 12 is a front perspective view of an alternative sandal according to an aspect of the disclosure.

As shown in FIGS. 11 and 12, a midsole 214,314 of the general configuration discussed above can be adapted for use as an outer for a sandal 210,319. In the example shown in FIG. 11, sandal 210 is in the general form of a flip-flop, and midsole 214 is configured in a similar manner to that which is shown in FIGS. 8-10, with the entire outer for sandal 210 comprising a molded resilin midsole 214, similar to midsole 114, discussed above, including of the above-described foamed resilin material. In this manner, midsole 214 can be made of a similar resilin material to that of midsole 114 to provide desired abrasion resistance, with potential adjustments for other unique features or desired characteristics for sandal 210. As shown, midsole 214 can be molded with a contoured footbed 276, including with a pronounced arch 264. Further, midsole 214 can be molded with holes 286 through which straps 288 can attach in a manner similar to other types of flip-flop style sandals.

In various implementations, holes 286 can be configured such that a disk- or T-shaped head of the straps 288 can be received within a portion thereof in a snap- or press-fit manner and/or to allow for permanent fixation by way of adhesive or the like. As also discussed above, midsole 214 can be molded with treads, similar to those shown in FIG. 10, in a pattern derived for the desired traction and stylistic considerations for sandal 210 such that no outsole is applied over midsole 214 or such that only small portions of outsole material are applied in specific areas of midsole 214, as also discussed above. The depicted straps 288 are exemplary only and can be configured differently for purposes of style and fit. Straps 288 may be of any number of materials or combinations thereof, including various plastics, including thermoplastic elastomer, rubber, leather (or leather alternatives such as mycelium material or the like), textile (both woven and various non-woven types), or molded or cut resilin material.

In an alternative embodiment, a flip-flop type sandal similar to that which is shown in FIG. 11 can made from cut sheet stock of resilin material in a laminated form similar to the midsole 14 used in connection with sneaker 10, as described above. In such an embodiment, the ends of straps 288 can be embedded between layers with holes 286 only extending partway through midsole 214.

A further embodiment of a sandal 310 is shown in FIG. 12, wherein sandal 310 is in the form of a slide with a single strap-style upper 312 affixed along the sidewalls 390 of midsole 314 from the medial side 358 to the lateral side 360 thereof. As further shown, sandal 310 can include an outer comprising midsole 314 of a resilin material (including of a foamed resilin material in whole or in part) and a separate outsole 316 bonded with midsole 314 to define the ground-contacting surface for sandal 310. In a similar manner to that which is discussed above with respect to FIG. 11, midsole 314 can be molded and can define a contoured footbed 376, which can, as illustrated, exhibit additional contour compared to footbed 276 in FIG. 11, although other configurations are possible.

As also shown in FIG. 12, upper 312 can extend between respective portions of midsole 314 and outsole 316, which can provide additional surface area for attachment of upper 312 to midsole 314 and outsole 316, which may be achieved by way of adhesives or the like. In one example, upper 312 can extend entirely beneath midsole 314 to connect the medial 358 and lateral 360 sides thereof, thereby further securing upper 312 to the assembled outer. In this and similar constructions, midsole 314 can be molded in such a way as to accommodate any portions of upper 312 that extend therebeneath. The depicted upper 312 can take a number of known alternative forms, consistent with the present disclosure, including by incorporating one or more straps with buckles or other adjustment mechanisms and may include an additional strap or the like to extend around the wearer's heel and/or a whole or partial enclosure over the wearer's toes (i.e., a clog). In any of these configurations, upper 312 can be made from any number of materials or combinations thereof, including various plastics, including thermoplastic elastomer, rubber, leather (or leather alternatives such as mycelium material or the like), textile (both woven and various non-woven types), or molded or cut resilin material.

Figure 13:
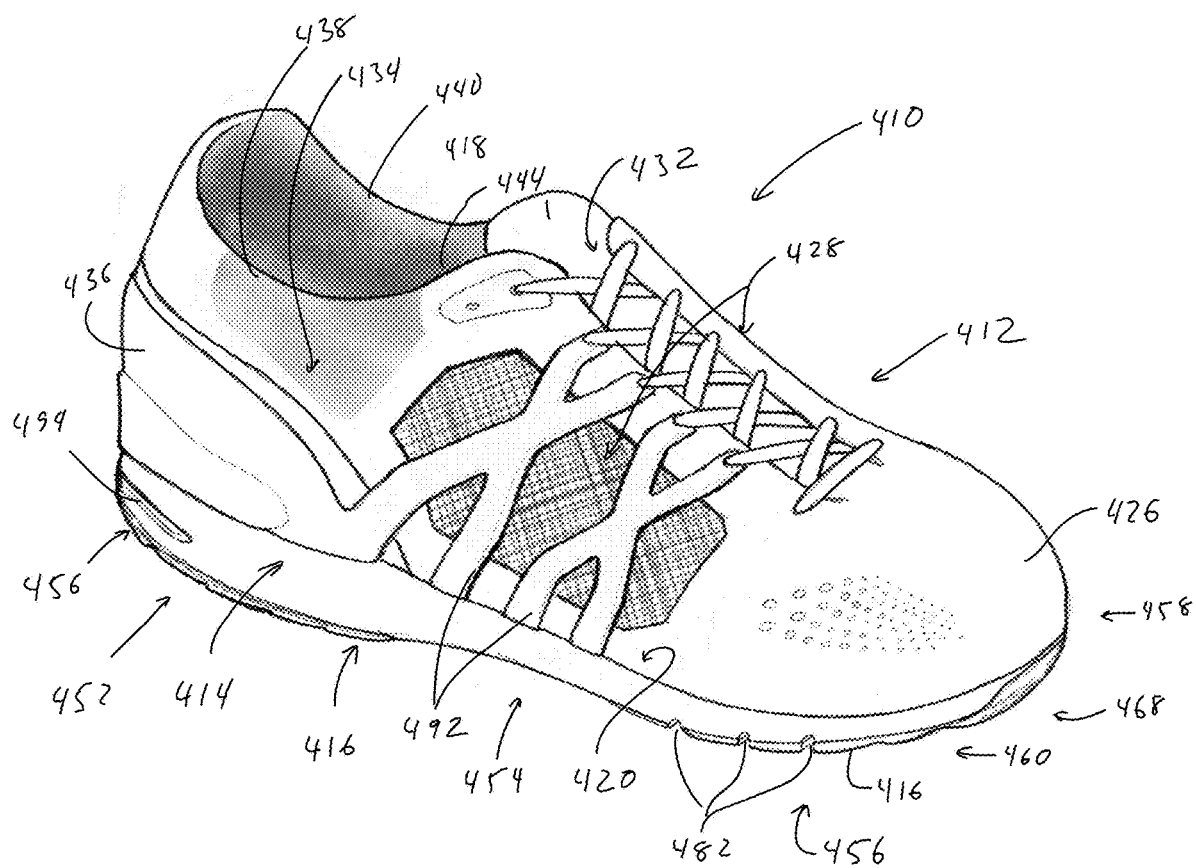
FIG. 13 is a front perspective view of a sneaker according to another aspect of the disclosure.
Figure 14:
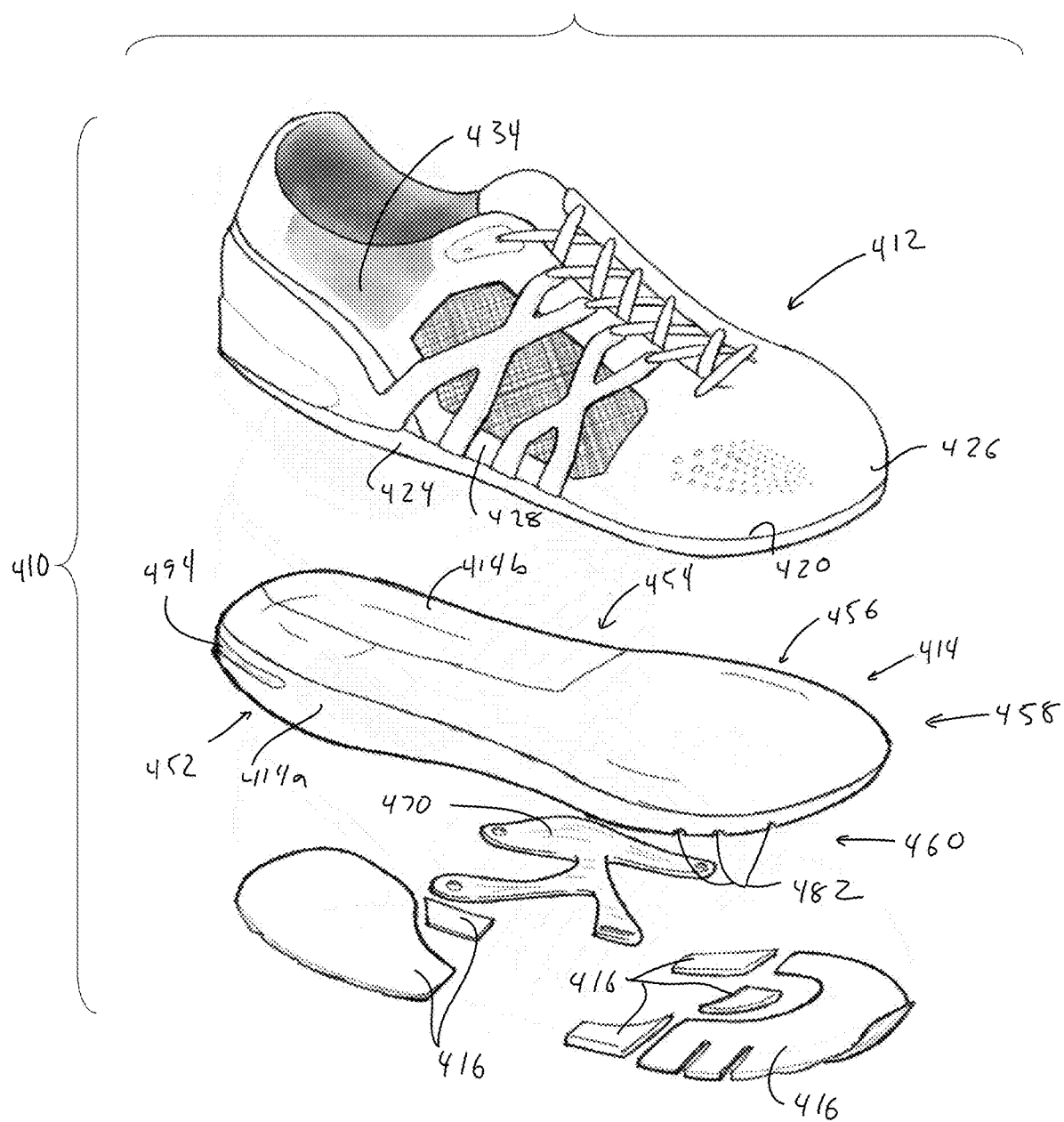
FIG. 14 is a front perspective exploded view of the sneaker.
Figure 15:
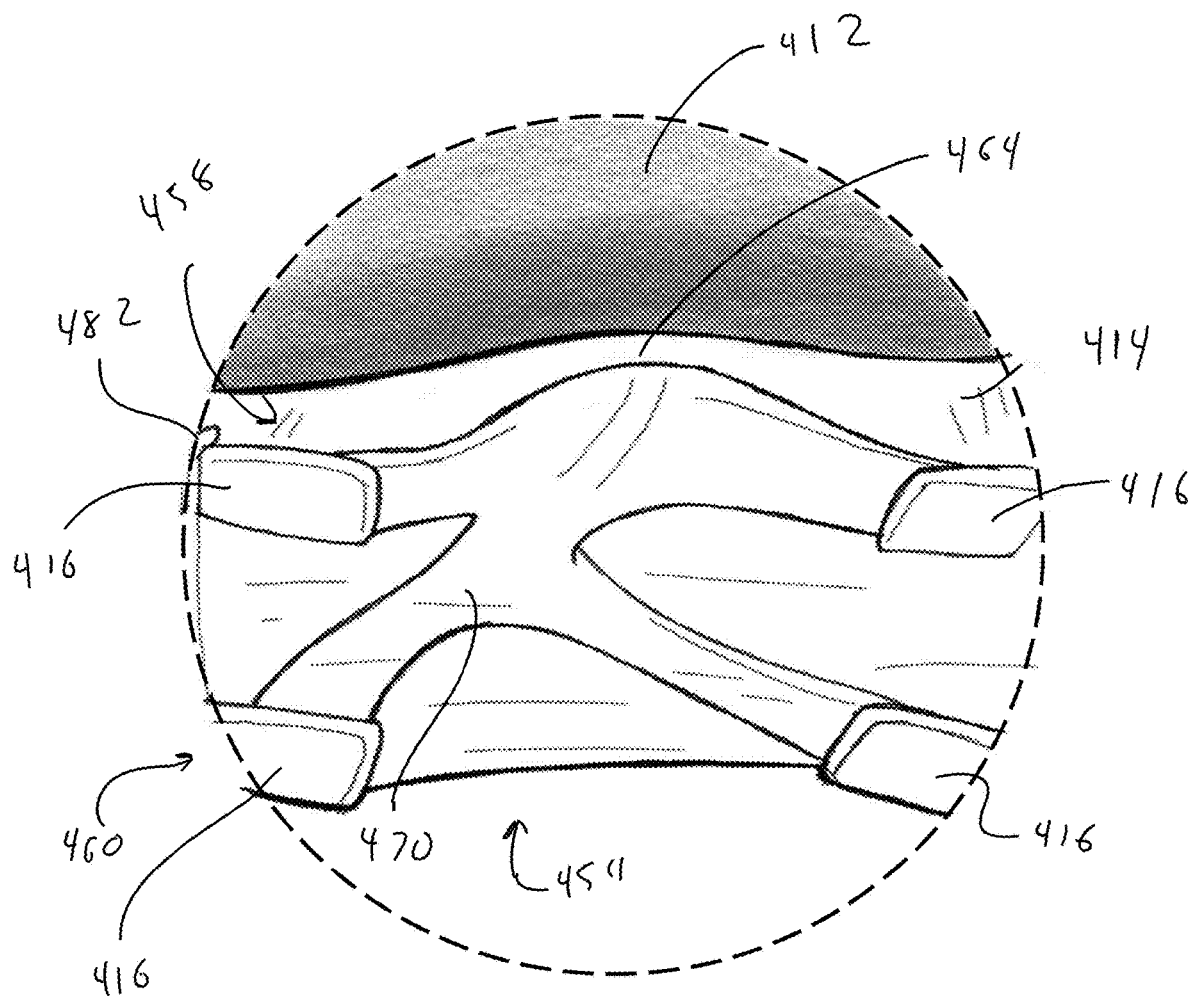
FIG. 15 is a bottom perspective view of a portion the sneaker.

Turning to FIGS. 13-15, a further example of a sneaker 410 is shown that incorporates a molded resilin midsole 414 generally similar to that which is discussed above with respect to FIGS. 8-10 incorporated into an athletic sneaker. In such an embodiment, the upper 412 may be configured to meet various performance-based criteria to make the sneaker 410 (and variations thereof) suitable for different athletic activities or combinations thereof according to various understood techniques and by incorporating various known features. Sneaker 410 according to the present embodiment can be so configured, such as by the general reduction in seams to decrease weight and increase flexibility, as well as by incorporating reinforcement 492 along the quarters 434 to help increase foot retention and stability. In the same manner, midsole 414 can be configured to provide various performance characteristics desired for various types of athletic activity over the overall cushioning and comfort that may be prioritized in implementations of midsole 14 and 114 for the lifestyle sneakers 10 and 110 discussed above with respect to FIGS. 1-10.

In one example, sneaker 410 can be adapted for running by providing a lightweight upper 412 with certain features promoting foot retention and allowing a tight fit without inducing discomfort. In such an arrangement, midsole 414 may be configured for reduced weight (including by allowing reduction in the amount of midsole 414 covered by outer 416, as discussed above). Further, midsole 414 may be configured to provide a degree of cushioning sufficient to reduce fatigue, but may promote return of such energy rather than dissipation. Various compositions of the resilin material described herein may be used to provide such energy return, including by the particular selection of the resilin composition and the cross-linking material and the non-aqueous solvent used for the solvent exchange step discussed above. Still further, various materials can be added to the resilin material prior to cross-linking to derive a composite material.

In one example, such an additive can include fumed silica representing between about 2% to about 20% of the total material (including resilin protein) used for midsole 414 by weight. In one embodiment, a resilin midsole can incorporate fumed silica at about 10% by total weight. This and other aggregate additives can increase the overall stiffness/rigidity of midsole 414 and can, similarly, increase the modulus of elasticity of the midsole 414 material. In a further example, a midsole 414 comprised of different specific resilin material compositions in different areas thereof can further promote suitability for various activities. In one example, a resilin material 414a of a relatively higher density can be used in the heel 452 and mid-foot 454 areas along the medial side 458, compared with a material 414b through the remaining midsole, including the lateral side 460 to provide for stability control, particular in the management of over-pronation during running. Other examples of such construction used in connection with prior foam midsoles can be similarly derived using various resilin material compositions. Additionally, resilin material can be molded over various non-resilin inserts 494, including those of various elastomers to promote cushioning in various areas (such as above the heel strike 462 and in the metatarsal head area 466 of the fore-foot 456). In some variations, such inserts 494 can be in an internal pocket within midsole 414 such that softer elastomers or even various liquids can be used for an insert 494 with appropriate protection thereof provided by midsole 414. Various other types of athletic sneakers can similarly incorporate midsoles of resilin material configured to provide characteristics desired by such activity, including for tennis, basketball, and the like.

As discussed above, the resilin material used for midsole 414 can be a foamed resilin material or a laminated perforated structure, according to the various examples and configurations discussed above. In this manner, the various portions of midsole 414a and 414b can be of foamed resilin materials having different properties (e.g. density) achieved by variations in the foam, including cell size or the like. In a further example, midsole 414 can be of a closed-cell foam structure that can be achieved, for example, by fabricating beads of resilin material (i.e. solid resilin material) according to various configurations for the desired properties thereof. The resilin beads can be placed into a mold for midsole 414 and re-crosslinked to join the beads together in the overall shape for midsole 414. In this arrangement, the beads can be of varying sizes in a generally spherical shape such that, when the beads are placed into the mold, voids are present between the beads with the beads achieving sufficient mutual contact to enclose cells by way of the voids. In this manner, beads of different sizes can be used together in a composite structure to provide the desired enclosed cell configuration. Further, different beads in different arrangements can be used in various areas of midsole 414 (including areas 414a and 414b, as shown in FIG. 14) to provide different properties for the closed cell resilin foam material.

As further shown in FIG. 15, midsole 414 can incorporate a molded external shank 470 that extends along a portion of the outer surface of midsole 414 and is anchored to portions of the midsole 414 underlying outsole 416. Such implementations of shank 470 can be of an injection molded polymer (i.e., various plastics), carbon fiber reinforced polymer, or Kevlar reinforced polymer and can be of various shapes to achieve desired performance and stylistic characteristics. Shank 470, as shown, can be fabricated separate from midsole 414 and can be affixed therewith using adhesives or the like with outsole 416 being subsequently assembled with midsole 414, including over shank 470. In another example, midsole 414 can be molded over shank 470 by positioning shank 470 in the midsole mold prior to the addition of the desired resilin protein and crosslinking thereof. In various implementations according to the illustrated midsole 414 and understood variations thereof, midsole 114 may include various flex-notches 482 to provide localized areas of increased flexibility, where desired.

Resilin material can be incorporated into additional types of footwear based on applications of the above principles. As discussed above, shoe insoles (e.g., insole 20) can be made of the present resilin material, including on the uppermost surface (due to the potential biocompatibility of resilin materials). Such insoles can incorporate reinforcement, including by molding resilin material over an insert or scrim to increase the strength of the insole and its resistance against tearing and the like. Insoles of variations of the present resilin materials can be utilized in practically any type of footwear, including dress shoes, work shoes, boots, etc. Still further, inserts of molded resilin material can be incorporated into various types of midsoles resembling or otherwise similar to existing types of midsoles. In one such example, a molded insert of resilin material optimized for cushioning can be incorporated into the interior of a dress shoe midsole, such as by the fabrication of a generally traditional midsole of leather or the like with an internal cavity for receiving the resilin insert therein in a concealed manner. Similar inserts can be similarly incorporated into other types of midsoles, including athletic midsoles of a foam material. Still further, a molded resilin material can be used as an outer for a dress shoe in a similar manner to the use of midsole 114 as the outer for the lifestyle sneaker 110, discussed above. Additionally, resilin materials of the types discussed herein can be used to replace various foams used elsewhere in various types of shoes, including within the tongues 30 and the collar 38 areas thereof or other areas where padding is incorporated therein.

As mentioned above, the shape and configuration of the above-described portions of the upper are exemplary only and can be altered to achieve different appearances, as well as different fit and performance characteristics (flexibility, support, weight, etc.).

In some respects, the properties of the resilin that are generally comparable to elastomers can allow the above assembly to be completed using the above techniques with parameters and equipment identical to or comparable to those used in assembly of sneaker midsoles of elastomer, resulting in a similar appearance and the efficiencies of using established techniques and existing machinery. In this respect, the resilin material is generally not thermoplastic such that molding is carried out in a different manner than with some typical elastomers. The resilin material, however, may be amenable to other processing and fabrication techniques used for elastomer that may be useful in fabricating the footwear disclosed herein.

It is to be appreciated that the above techniques and fabrication methods using the resilin material can also be used to fabricate other types of footwear, including the various types (slippers, sandals, moccasins, boat shoes) mentioned above by using techniques generally similar to those used to make portions of such footwear from elastomers, while taking advantage of the numerous additional properties of the resilin material to provide additional benefits for such footwear and the construction thereof according to the principles and variations described above. In this manner, the midsoles of various styles of dress shoes, boots, and the like can also be made of the present resilin material. In one application, resilin material may be derived and processed to resemble a "crepe sole" that is used in certain styles of boots (e.g., desert boots) and dress-shoes. Other similar applications are also possible.

It will be understood by one having ordinary skill in the art that construction of the described device and other components is not limited to any specific material. Other exemplary embodiments of the device disclosed herein may be formed from a wide variety of materials, unless described otherwise herein.

It is also important to note that the construction and arrangement of the elements of the articles, as shown, in the examples above are illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the examples shown in the drawings and described above are merely for illustrative purposes and not intended to limit the scope of the article, which is defined by the following claims as interpreted according to the principles of patent law, including the Doctrine of Equivalents.

What is claimed is:

1. An article of footwear, comprising:
   an upper; and
   a midsole coupled with the upper;
   wherein the midsole includes at least a portion of a solid resilin material comprising a cross-linked recombinant resilin and a polar nonaqueous solvent.

2. The article of footwear of claim 1, wherein the midsole defines at least one exposed ground-contacting surface at least in one of the heel or fore-foot areas of the midsole.

3. The article of footwear of claim 2, wherein the at least one exposed ground contacting surface is uncovered by an outsole and includes at least one tread of the solid resilin material molded with the midsole.

4. The article of footwear of claim 1, wherein the polar nonaqueous solvent is glycerol.

5. The article of footwear of claim 1, wherein the solid resilin material is coated with an encapsulant material.

6. The article of footwear of claim 1, wherein the midsole includes a shank embedded within the solid resilin material.

7. The article of footwear of claim 1, wherein:
   the article of footwear is a sandal; and
   the upper includes one or more straps and defines at least one open area.

8. The article of footwear of claim 1, wherein the midsole comprises a plurality of portions of the resilin material, at least some of the plurality of portions having different physical properties selected to correlate with at least one characteristic of the corresponding locations of the at least some of the portions within the midsole.

9. The article of footwear of claim 8, wherein a first one of the portions of the resilin material is positioned within a heel area of the midsole and exhibits a higher density compared to at least a second one of the portions positioned within a fore-foot area of the midsole.

10. The article of footwear of claim 1, wherein the midsole comprises a plurality of discrete portions of the solid resilin material assembled together by at least one of a cross-linking solution or an adhesive.

11. The article of footwear of claim 1, wherein the midsole is comprised of a single, molded piece of the solid resilin material.

12. The article of footwear of claim 1, further including an insole received within the upper above the midsole, wherein the insole includes at least a portion of the solid resilin material comprising the cross-linked recombinant resilin and the polar nonaqueous solvent.

13. The article of footwear of claim 1, wherein the solid resilin material is a foamed resilin material having a plurality of cells distributed in a matrix of the solid resilin material.

14. The article of footwear of claim 1, wherein the midsole comprises a plurality of portions of the foamed resilin material including different sizes of cells distributed in the respective matrices of the solid resilin material resulting in the plurality of portions of the foamed resilin material having different relative densities.

15. An insole for an article of footwear, comprising:
   a solid resilin material comprising a cross-linked recombinant resilin and a polar nonaqueous solvent defining at least a portion of the insole.

16. The insole of claim 15, wherein the portion of the insole comprising the solid resilin material includes an exposed foot-supporting surface.

17. The insole of claim 16, wherein the solid resilin material is molded over one of an insert or a scrim.

18. The insole of claim 15, wherein the portion of the insole comprising the solid resilin material extends around at least a perimeter of the insole.

\* \* \* \* \*